US009598676B2

(12) United States Patent
Vadrevu et al.

(10) Patent No.: US 9,598,676 B2
(45) Date of Patent: Mar. 21, 2017

(54) COMPOSITION USEFUL AS ROTAVIRUS VACCINE AND A METHOD THEREFOR

(75) Inventors: Krishna Mohan Vadrevu, Hyderabad (IN); Selvi Veerabadran, Hyderabad (IN); Sai Devarajulu Prasad, Hyderabad (IN)

(73) Assignee: Bharat Biotech International Limited (IN)

( * ) Notice: Subject to any disclaimer, the term of this patent is extended or adjusted under 35 U.S.C. 154(b) by 0 days.

(21) Appl. No.: 13/383,629

(22) PCT Filed: Jan. 25, 2010

(86) PCT No.: PCT/IN2010/000041

§ 371 (c)(1), (2), (4) Date: Jan. 12, 2012

(87) PCT Pub. No.: WO2011/007363

PCT Pub. Date: Jan. 20, 2011

(65) Prior Publication Data

US 2012/0107356 A1 May 3, 2012

(30) Foreign Application Priority Data

Jul. 13, 2009 (IN) .......................... 1649/CHE/2009

(51) Int. Cl.

| | |
|---|---|
| ***C12N 7/02*** | (2006.01) |
| ***A61K 39/02*** | (2006.01) |
| ***A61K 39/145*** | (2006.01) |
| ***A61K 39/155*** | (2006.01) |
| ***A61P 37/04*** | (2006.01) |
| ***C12N 7/00*** | (2006.01) |
| ***A61K 39/15*** | (2006.01) |
| ***A61K 39/12*** | (2006.01) |
| *A61K 39/00* | (2006.01) |

(52) U.S. Cl.

CPC ................ *C12N 7/00* (2013.01); *A61K 39/12* (2013.01); *A61K 39/15* (2013.01); *A61K 2039/5254* (2013.01); *C12N 2720/12334* (2013.01); *C12N 2720/12351* (2013.01); *C12N 2999/007* (2013.01)

(58) Field of Classification Search

CPC .. A61K 2300/00; A61K 31/337; A61K 31/70; A61K 31/7088; A61K 39/00

USPC ........................................................ 424/215

See application file for complete search history.

(56) References Cited

U.S. PATENT DOCUMENTS

| | | | | |
|---|---|---|---|---|
| 6,210,683 | B1 * | 4/2001 | Burke et al. | 424/230.1 |
| 7,101,569 | B2 * | 9/2006 | Franz et al. | 424/439 |
| 2009/0155351 | A1 * | 6/2009 | Hejl et al. | 424/451 |

FOREIGN PATENT DOCUMENTS

| | | | |
|---|---|---|---|
| EP | 0947581 | A1 | 10/1999 |
| WO | 0112797 | A2 | 2/2001 |
| WO | 0211540 | A1 | 2/2002 |
| WO | 2005058356 | A2 | 6/2005 |
| WO | WO2005058356 | * | 6/2005 |
| WO | 2007132480 | A2 | 11/2007 |
| WO | WO2007132480 | * | 11/2007 |

OTHER PUBLICATIONS

International Search Report dated Jul. 6, 2010, World Intellectual Property Organization (WIPO), PCT/IN2010/000041.

International Preliminary Report on Patentability dated Jan. 17, 2012, World Intellectual Property Organization (WIPO), PCT/IN2010/000041.

Choppin et al., “Multiplication of a Myxovirus (SV5) with Minimal Cytopathic Effects and Without Interference”, Virology, Academic Press, Jun. 1, 1964, Orlando, pp. 224-233.

Scott et al., “Enhanced Yields of Measles Virus from Cultured Cells”, Journal of Virological Methods, Elsevier BV, vol. 5, No. 3/04, Nov. 1, 1982, pp. 173-179.

Barrett et al., “Vero Cell Platform in Vaccine Production: Moving Towards Cell Culture-Based Viral Vaccines”, Expert Review of Vaccines, vol. 8, No. 5, May 1, 2009, pp. 607-618.

* cited by examiner

*Primary Examiner* — Janet L Andres
*Assistant Examiner* — Barry A Chestnut
(74) *Attorney, Agent, or Firm* — Emerson, Thomson & Bennett, LLC; Roger D. Emerson

(57) ABSTRACT

Compositions and methods related to live or live attenuated pre-conditioned and typical viruses such as rotaviruses are disclosed. The live attenuated rotaviruses exhibit better stability characteristics and are useful for the prevention of a rotavirus infection and/or rotavirus gastroenteritis in children.

3 Claims, 24 Drawing Sheets

COMPOSITION USEFUL AS ROTAVIRUS VACCINE AND A METHOD THEREFOR

FIELD OF THE INVENTION

The present invention relates to vaccine formulations containing rotaviruses capable of exhibiting higher titer value, improved stability characteristics. The formulation may be in liquid or lyophilized form and exhibit enhanced shelf life while retaining its therapeutic efficacy. The invention also relates to methods of producing such viruses and methods for preparing such formulations. The invention further relates to prophylactic and therapeutic methods for their use.

BACKGROUND OF THE INVENTION

There are a number of human antiviral vaccines that are currently in use. These include Hepatitis A virus, Hepatitis B virus, Influenza virus, Japanese B encephalitis virus, Measles, Mumps, Rubella (MMR) virus, Poliovirus virus, Rabies virus, Smallpox, Varicella-Zoster, Yellow fever virus vaccines. In addition to the growing number of vaccine products, there are different compositions or formulations in use or being developed for a given vaccine. The successful use of live viral vaccines depends not only on the proper choice and delivery of the virus, but also on maintaining the sufficient titer or potency required for an immune response. The inherent lability of live viruses presents a particular formulation challenge in terms of stabilizing and preserving vaccine viability during manufacturing, storage, and administration. There are a number of formulations known in the art for rotavirus vaccines but suffer from one or the other problems with regard to stability during storage.

Rotavirus is a genus of double-stranded RNA viruses in the family Reoviridae and is transmitted by the faecal-oral route. It infects cells that line the small intestine and produces an enterotoxin, which induces gastroenteritis, leading to severe diarrhea and sometimes death through dehydration. Rotavirus infection is the greatest cause of diarrhea-related deaths among infants and young children. Every year, rotavirus gastroenteritis causes the death of 310,000-590,000 infants and young children worldwide.

All rotavirus vaccines developed to date have been based on live rotavirus strains that have been isolated from humans or animals and in vitro reassorted, adapted to cell cultures, and then formulated for oral delivery. Both monovalent and multivalent animal-based strains have demonstrated efficacy as candidate vaccines.

The human rotavirus strain 116E, a natural human-bovine reassortant and naturally attenuated, is a human G9 strain into which a single bovine VP4 gene (VP=viral protein), homologous to the P[11] gene segment, was naturally introduced. The I132 strain, also named G10P [11], is primarily composed of bovine genes and has only two gene segments of human origin, VP5 and VP7. These two rotavirus vaccine strains have been individually prepared as pilot lots of monovalent oral rotavirus vaccine liquid formulations for clinical trials to be conducted in India.

Bharat Biotech International Ltd. (BBIL) obtained the human rotavirus strains, 116E and I321 from National Institute of Health (NIH) under the material transfer agreement with National Institute of Allergy and Infectious Diseases (NIAID), NIH, Bethesda, USA. The original 116E (G9[P11]) and I321 (G10P[11]) were adapted to grow in cell culture by passages in primary African green monkey kidney (AGMK) cells then in MA104 cell substrate and later in serially Passaged AGMK (SPAGMK). MA104 and SPAGMK cell substrates are not approved by National Regulatory Authorities (NRA) for commercial vaccine production. Hence it is preferable to adapt 116E and I321 and other rotavirus vaccine strains to approved, certified, licensed and fully characterized cell substrate like Vero cell substrate and/or human diploid cells like MRC-5.

The prior art known to the applicant includes WO 02/11540 A1 describes rotavirus vaccine formulations, which include buffering agents appropriate for oral administration of rotavirus vaccines. The formulations disclosed in WO 02/11540 A1 also include compounds to stabilize the vaccine compositions against potency loss. More specifically, the compositions disclosed in WO 02/11540 require a sugar, phosphate and at least one carboxylate at least one human serum albumin or amino acid selected from glutamate, glutamin and arginin. However, the stabilities achieved varied greatly, especially at temperatures over 20° C. appear to show considerable losses in potency with the formulations of WO 02/11540 A1.

WO 99/62500 ('500), WO 2005/058356 ('356) A 2 and WO 2001/012797 ('197) discloses using vaccine stabilizers for preparing vaccine formulations and lyophilized vaccines, storage stable virus compositions, method of separating rotavirus variants and live attenuated rotavirus Liquid Vaccine. '500 discloses measles-mumps-rubella lyophilised vaccine prepared employing stabilizer consisting of hydrolysed gelatin, sorbitol, phosphate, sodium chloride, sucrose, bicarbonate, glucose human serum albumin and citrate. The invention banks upon dual presence of increased amount of a disaccharide and polyhydric alcohol at pH between 6.0 and 7.0 for thermo-stability.

Despite requiring number of ingredients making the invention cost extensive, fails to achieve stability at ambient temperatures. This in turn adds to the requirement of special infrastructure for storing the vaccine making the invention further costly. However, most of these formulations offer limited storage stability and thus are not commercially viable.

PCT/IN07/00190 titled A Composition Useful as a Vaccine discloses a stable vaccine The essence of the invention centers around the combined effect of the first protein that is human serum albumin, the second protein, which is at least partially hydrolyzed and a combination of three different sugars. Additionally, the inventions also rely on inclusion of trypsin in the culture medium during adaptation of viruses. The claimed vaccine is stable for 3 weeks at 37° C., six months at 25° C., and one year at 2° C.-8° C.

It is apparent from the foregoing description that despite these advances in area of vaccine formulation, there remains a distinct need for live commercially viable viral vaccine with improved thermo-stability and shelf life.

The present invention fulfills this need by providing live or live attenuated virus that exhibits better and improved stability characteristics whether in the form of a pooled bulk from three single harvests of the virus from the same batch, or in a liquid or lyophilized formulation. Stability with reference to the virus (e.g., rotavirus or rotavirus vaccine) herein shall mean viral titer at a given point in time starting from the time of harvest from the cultured cells through the bulk stage to the formulated vaccine. The inventors after prolonged research could develop a composition of the present invention useful as a vaccine that exhibit enhanced stability of the bulk and formulated particularly at ambient temperature.

An improved stability, in statistically significant terms, can be achieved by the use of the virus that has come in contact with or been exposed to human serum albumin during the virus growth and multiplication stage in cell cultures. For purposes of this invention, the virus is deemed to come in contact with or be exposed to human serum albumin when the virus infected host cells are propagated in a cell culture medium/growth medium supplemented with human serum albumin. The virus or virus population that has been so exposed to human serum albumin is referred to as a "pre-conditioned" virus. The virus that has not been so exposed to the human serum albumin is referred to as a "typical virus" herein. The pre-conditioned virus whether at the bulk stage or in the form of a formulation, i.e., a vaccine/formulated vaccine, exhibits better stability (in statistically significant terms) than the typical virus.

The present invention further discloses that the stability of the virus, whether it is the pre-conditioned virus or the typical virus, in a formulation can also be further improved or at least sustained i.e., the stability can be maintained or, at a minimum, delayed from gradually reaching nil or zero stability during storage by practicing systems (i) and (ii): According to system (i), to realize improved or sustained stability, the virus is formulated with a non-viral protein or protein hydrolysate thereof or a vegetable protein or an analogous protein such as human serum albumin. The hydrolysate can be exemplified but not limited to lactalbumin hydrolysate, yeast hydrolysate, peptone, gelatin hydrolysate, and egg protein hydrolysate. The vegetable protein includes but not restricted to corn protein, wheat protein, garbanzo bean protein, kidney bean protein, lentil protein, lima bean protein, navy bean protein, soybean protein, split pea protein. Human serum albumin is of natural or recombinant origin. The virus is formulated with the non-viral protein or protein hydrolysate thereof simply by supplementing the formulation used for making the vaccine with the non-viral protein or protein hydrolysate thereof. This system (i) is understood to mean a single component system. According to system (ii), the virus is contacted with a non-viral protein or protein hydrolysate thereof as in the single component system, and 1-2 disaccharides by supplementing the formulation used for making the vaccine with protein or protein hydrolysate and 1-2 disaccharides. This system (ii) is understood to mean a two or three component system depending on whether the formulation containing virus is supplemented with a single disaccharide (two component system) or a combination of two different disaccharides (three component system). By practicing system (ii), the stability levels seen in the single component system is further improved.

Thus, in one general aspect, the present invention discloses compositions containing pre-conditioned virus or typical virus exhibiting improved and/or sustained stability.

The novelty of the invention resides in supplementing the culture medium with human serum albumin while propagating virus to achieve the viral antigen and vaccine formulation with enhanced titer value, shelf life, and thermostability even without supplementation of stabilizers. The shelf life can be further enhanced with addition of stabilizers as disclosed herein before. This leads to a therapeutically better vaccine adopting simple cost effective commercially viable process. In addition to technical advancement, the invention also qualifies the acid test of economic significance.

Object of the Invention

The main object of the present invention to provide a composition useful as rotavirus vaccine having increased shelf life obviating the drawbacks of the relevant prior art.

The other object is to provide vaccine formulations containing live attenuated rotaviruses capable of exhibiting higher titer value, improved stability characteristics at ambient temperatures.

The formulation may be in liquid or lyophilized form and exhibit enhanced shelf life while retaining its therapeutic efficacy/potency.

The invention also relates to methods of producing such viruses and methods for preparing such formulations.

The invention further relates to prophylactic and therapeutic methods for curbing rotavirus infections administering the vaccine formulations to the subjects suffering from such infections.

BRIEF DESCRIPTION OF THE DRAWINGS

The viral titer mentioned in the figures correspond to Focus-Forming Units (FFU) per 0.5 ml of rotavirus 116 E harvest or final bulk and formulated vaccine. In the various figures herein, the reference to Bioprocess 1 represents that the starting material used is the typical virus and the reference to Bioprocess 2 represents that the starting material used is the pre-conditioned virus. Unless specified otherwise, the data in the figures represent stability for the pre-conditioned virus. FIGS. 1-12H show data for liquid formulations (Liq=liquid)

FIG. 1 shows the average titer obtained from the harvests of Bioprocess 1 (typical virus) and Bioprocess 2 (pre-conditioned virus) in five experiments.

FIG. 2 shows stability data for the viral harvests, typical virus (Bioprocess 1) and pre-conditioned virus (Bioprocess 2), each in the absence (FIG. 2A) or presence (FIG. 2B) of stabilizers, viz., 5% LAH, 80% sucrose and 0.5% trehalose, in the liquid formulation at 37° C.

FIG. 3 (Liq) shows stability data for the pre-conditioned virus in four different formulations at 2-8° C. (3A), 25° C. (3B) and 37° C. (3C). In each case: series 1 refers to a formulation with 2.5% lactalbumin hydrolysate; series 2 refers to a formulation with 10% lactalbumin hydrolysate, and 0.5% trehalose; series 3 refers to a formulation with 20% lactalbumin hydrolysate; and series 4 refers to a formulation with the combination of 2.5% lactalbumin hydrolysate, 0.5% of starch and 0.5% of trehalose.

FIG. 4 (Liq) shows the stability data for the rotavirus in a formulation with and without 5% lactalbumin hydrolysate+80% sucrose+0.5% trehalose kept at 2-8° C. (4A), 25° C. (4B) and 37° C. (4C).

FIG. 5 (Liq) show s stability data for the rotavirus in four different formulations at 2-8° C. (5A), 25° C. (5B) and 37° C. (5C). In each case: series 1 refers to a formulation containing the combination of 20% lactalbumin hydrolysate, and 0.5% of trehalose; series 2 refers to a formulation containing the combination of 10% lactalbumin hydrolysate, 1.0% of lactose; series 3 refers to a formulation containing the combination of 5% lactalbumin hydrolysate, 80% of sucrose; and series 4 refers to a formulation containing the combination of 10% lactalbumin hydrolysate and 50% of maltose.

FIG. 6 (Liq) shows stability data for the rotavirus in four different formulations at 2-8° C. (6A), 25° C. (6B) and 37° C. (6C). In each case: series 1 refers to a formulation containing the combination of 0.5% lactalbumin hydrolysate, 10% of soy protein and 1.0% of trehalose; series 2 refers to a formulation with the combination of 0.5% lactalbumin hydrolysate, 10% of soy protein and 1.0% of lactose; series 3 refers to a formulation with the combination of 5% lactalbumin hydrolysate, 2.5% of soy protein and 80% of sucrose; and series 4 refers to a formulation with the combination of 5% lactalbumin hydrolysate, 2.5% of soy protein and 50% of maltose.

FIG. 7 (Liq) shows high stability data for the rotavirus in four different formulations at 2-8° C. (7A), 25° C. (7B) and 37° C. (7C). In each case: series 1 refers to a formulation containing the combination of 10% lactalbumin hydrolysate, 10% of sucrose and 1.0% of trehalose; series 2 refers to a formulation containing the combination of 10% lactalbumin hydrolysate, 5% of maltose and 1.0% of trehalose; series 3 refers to a formulation containing the combination of 2.5% lactalbumin hydrolysate, 80% of sucrose and 1% of trehalose; and series 4 refers to a formulation containing the combination of 2.5% lactalbumin hvdrolysate, 50% of maltose and 1% of trehalose.

FIG. 8 (Liq) shows stability data for the rotavirus in four different formulations at 2-8° C. (8A), 25° C. (8B) and 37° C. (8C). In each case: series 1 refers to a formulation with the combination of the typical virus, 5% of lactalbumin hydrolysate, 80% of sucrose and 0.5% of trehalose; series 2 refers to a formulation containing the combination of the pre-conditioned virus, 5% lactalbumin hydrolysate, 80% of sucrose and 0.5% of trehalose; series 3 refers to a formulation with the combination of the typical virus, 0.1% of recombinant human serum albumin (rHSA) and 80% of sucrose, and 0.5% of trehalose; series 4 refers to a formulation with the combination of the pre-conditioned virus, 0.1% of rHSA, 80% of sucrose and 0.5% of trehalose; series 5 refers to a formulation containing the combination of the typical virus, 80% of sucrose and 0.5% of trehalose; and series 6 refers to a formulation containing the combination of the pre-conditioned virus, 80% of sucrose and 0.5% of trehalose.

FIG. 9 (Liq) shows the stability data for the rotavirus in five different formulations at 37° C.

FIG. 10 (Liq) shows the stability for the low titer rotavirus in five different formulations at 2-8° C. (10A) and 37° C. (10B).

FIG. 12H (Liq) shows stability data for typical rota virus formulations containing a combination of 20% Yeast hydrolysate, 5% Maltose, and 0.5% Lactose at 2-8° C., 25° C., and 37° C.

FIG. 13 (Lyo) shows the stability data for the rotavirus in four different lyophilized formulations at 2-8° C. (13A), 25° C. (13B) and 37° C. (13C). In each case: series 1 refers to the formulation with 0.5% human serum albumin and 12% sucrose; series 2 refers to the formulation with 0.5% lactalbumin hydrolysate, 0.5% trehalose; series 3 refers to the formulation with 0.5% soya protein and 0.5% trehalose; and series 4 refers to 0.25% polyvinyl pyrollidine, 0.5% trehalose.

FIG. 14 (Lyo) shows the stability data for the rotavirus in four different lyophilized formulations at 2-8° C. (14A), 25° C. (14B) and 37° C. (14C). In each case: series 1 refers to the formulation with 0.5% human serum albumin, 12% of sucrose and 0.1% of starch; series 2 refers to the formulation with 0.5% lactalbumin hydrolysate, 0.5% trehalose and 0.1% starch; series 3 refers to the formulation with 0.5% soyaprotein 0.5% trehalose and 0.1% starch; and series 4 refers to 0.25% polyvinyl pyrollidine, 0.5% trehalose and 0.1% of starch.

FIG. 15 (Lyo) shows the stability data for the rotavirus in four different lyophilized formulations at 2-8° C. (15A), 25° C. (15B) and 37° C. (15C). In each case: series 1 refers to the formulation with 0.5% human serum albumin, 12% of sucrose, 0.1% of starch and 304 mM bicarbonate; series 2 refers to the formulation with 0.5% lactalbumin hydrolysate, 0.5% trehalose, 0.1% starch and 304 mM bicarbonate; series 3 refers to the formulation with 0.5% soyaprotein 0.5% trehalose, 0.1% starch and 304 mM bicarbonate; series 4 refers to 0.25% polyvinyl pyrollidine, 0.5% trehalose, 0.1% of starch and 304 mM of bicarbonate.

FIG. 16 (Lyo) shows the stability data for the rotavirus in four different lyophilized formulations at 2-8° C. (16A), 25° C. (16B) and 37° C. (16C). In each case: series 1 refers to the formulation with 0.5% human serum albumin, 12% of sucrose and 0.1% of gum acacia; series 2 refers to the formulation with 0.5% lactalbumin hydrolysate, 0.5% trehalose and 0.1% gum acacia; series 3 refers to the formulation with 0.5% soyaprotein 0.5% trehalose and 0.1% gum acacia; and series 4 refers to 0.25% polyvinyl pyrollidine, 0.5% trehalose and 0.1% gum acacia.

FIG. 17 (Lyo) shows the stability data for the rotavirus in four different lyophilized formulations at 2-8° C. (17A), 25° C. (17B) and 37° C. (17C). In each case: series 1 refers to the formulation with 0.5% lactalbumin hydrolysate, 0.25% of polyvinyl pyrollidine; series 2 refers to the formulation with 0.5% lactalbumin hydrolysate, and 0.1% gum acacia; series 3 refers to the formulation with 0.5% lactalbumin hydrolysate and 0.1% pyridoxine HCL; and series 4 refers to 0.5% lactalbumin hydrolysate, and 0.1% starch.

SUMMARY OF THE INVENTION

Figure 1:
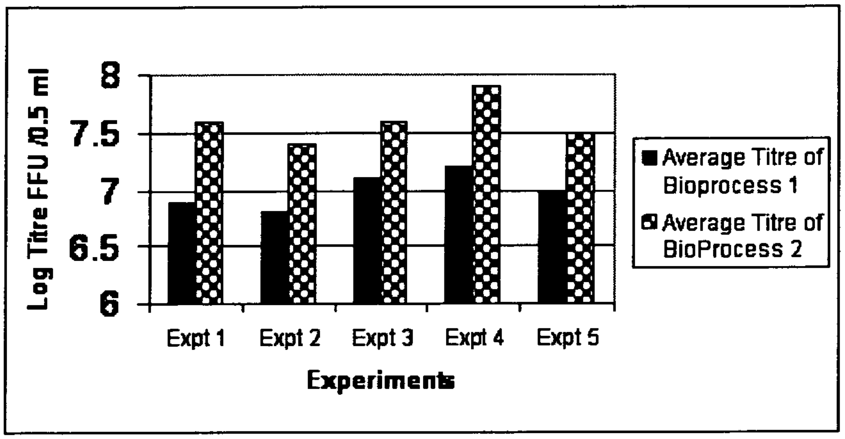

Accordingly the present invention provides a composition comprising:

(a) a viral antigen that is a live attenuated rotavirus and (b) a pharmaceutically acceptable buffer of physiological pH, wherein, the stability of the composition with respect to viral titer is enhanced in that the effect of propagating virus in presence of human serum albumin on stability is greater than the one propagated in absence of human serum albumin.

According to one of the embodiments. the composition further may comprise of at least one of the stabilizers comprising a non-viral protein or at least partially hydrolysed protein hydrolysate thereof or single disaccharides or combination of 2 disaccharides.

The non-viral protein or protein hydrolysate may be such as lactalbumin hydrolysate, yeast hydrolysate, gelatin hydrolysate, egg protein hydrolysate, hydrolysed peptone or vegetable protein selected from corn protein, wheat protein, garbanzo bean protein, kidney bean protein, lentil protein, lima bean protein, navy bean protein, soybean protein, split pea protein or an analogous protein exemplified by human serum albumin preferably lactalbumin hydrolysate or hydrolysed Soy protein more preferably lactalbumin hydrolysate.

According to other embodiments, the disaccharide employed may be such as trehalose or a combination of 2 disaccharides comprising of sucrose and trehalose.

A composition of the present invention thus may be comprising of (a) a viral antigen that is a live attenuated rotavirus, (b) a pharmaceutically acceptable buffer of physiological pH, and (c) non-viral protein or protein hydrolysate The composition as disclosed herein above may comprising (i) a viral antigen that is a live attenuated rotavirus as herein before disclosed at a titer ranging from $10^3$ to $10^{8.5}$ FFU/0.5 ml, (ii) a pharmaceutically acceptable buffer being phosphate-citrate buffer (310/100 mM) of pH 6.8 to 8.0 as a diluent/carrier, (iii) protein hydrolysate being lactalbumin hydrolysate in the range of 20-30% w/v and (iv) disaccharide being trehalose about 0.5% w/v or sucrose about 80% w/v and other disaccharide being trehalose about 0.5% w/v.

The composition comprises a live attenuated rotavirus capable of exhibiting a minimum of 0.8 log to a maximum of 1.1 logs per ml enhanced titer on average on storage at ambient conditions as compared to a live attenuated rotavirus propagated in absence of human serum albumin.

Further, the said live attenuated rotavirus is propagated in presence of 0.1% recombinant human serum albumin.

According to another aspect of the invention there also be provided a method for producing a live attenuated rotavirus of claim 1 comprising:

(i) infecting host cells with a live attenuated rotavirus;

(ii) growing the infected cells in a cell culture medium capable of supporting the growth of said cells, wherein said medium is supplemented with a human serum albumin and harvesting the said rotavirus capable of exhibiting better stability.

In one specific aspect the present invention discloses a composition containing a live and pre-conditioned virus (or virus population) with a given stability, wherein the stability of the virus is characterized by comparing to a live typical virus (or virus population) that is not propagated in presence of human serum albumin (designated as pre-conditioned) and shows a loss of log 4 titer greater than the difference between 4.5 and 7.5 FFU/0.5 ml, when both the compositions with live pre-conditioned virus or the live typical virus each are stored at 37° C. for four weeks after harvest. The composition contains a pharmaceutically acceptable buffer with or without a supplemental stabilizer such as a protein hydrolysate, a peptone, a vegetable protein or a disaccharide in the formulation. In another specific aspect, the present invention discloses a composition containing a live and pre-conditioned virus (or virus population) capable of exhibiting a minimum of 0.8 log to a maximum of 1.1 logs per ml enhanced titer on average on storage at ambient conditions as compared to a live typical virus, and a pharmaceutically acceptable buffer, and the pre-conditioned virus is capable of exhibiting the titer without any supplemental stabilizer such as a non-viral protein hydrolysate, a peptone, a vegetable protein and a disaccharide, in the composition.

In each of the above aspects to the extent a supplemental stabilizer is contemplated, lactalbumin hydrolysate is the most preferred supplemental stabilizer. A disaccharide (e.g., trehalose) or a combination of different disaccharides (e.g., sucrose and trehalose) is the next preferred stabilizer in a composition containing lactalbumin hydrolysate. In one embodiment, lactalbumin hydrolysate in the composition is at about 5% w/v, sucrose is at about 80% w/v and trehalose is at about 0.5% w/v. The composition may contain recombinant human serum albumin (e.g., 0.1% w/v) as a further supplemental stabilizer.

In one embodiment, the virus is a live rotavirus, such as a live attenuated rotavirus. Preferably, the live virus is a human live virus, such as human rotavirus. In a particularly preferred embodiment, the human rotavirus is rotavirus strain 116E or I 321. The composition according to the present invention is a vaccine. In an embodiment, the composition according to the present invention can have a live attenuated rotavirus at a titer in the range of from $10^3$ to $10^{8.5}$ FFU/0.5 ml. The live rotavirus is the preconditioned rotavirus.

In another general aspect, a method for producing a live attenuated pre-conditioned rotavirus is provided. It involves steps of infecting host cells with a live attenuated rotavirus, growing the infected cells in a cell culture medium supplemented with a human serum albumin and capable of supporting the growth of the cells and harvesting the pre-conditioned rotavirus. The harvested pre-conditioned rotavirus exhibits better stability as compared to a non pre-conditioned or typical virus.

In yet another general aspect, the present invention also discloses a method of adapting virus to a suitable cell substrate, such as Vero cells, serially passaging through the suitable medium, each passage occurring in a medium in the absence or presence of human serum albumin originated from human or recombinant human serum albumin.

DETAILED DESCRIPTION OF THE INVENTION

This invention concerns compositions and methods related to live attenuated rotaviruses. The live attenuated rotaviruses exhibit improved stability characteristics and are useful for the prevention of a rotavirus infection and/or rotavirus gastroenteritis in children.

In particular, this invention discloses various approaches and systems for providing rotavirus compositions which exhibit improved stability at a given point in time and sustained stability over a period of time during storage. One approach is the use of pre-conditioned viruses as the starting material in the compositions of the invention. Another approach is the use of various stabilizers to obtain improved stability when the virus used is a pre-conditioned virus.

As defined above, the virus or virus population harvested from cell cultures propagated in a medium containing human serum albumin is said to be a "pre-conditioned" virus or virus population. Conversely, the virus or virus population harvested from cell cultures in a medium not containing human serum albumin is said to be a "typical" virus or virus population. The live attenuated rotavirus is sometimes referred to herein as viral antigen or vaccine antigen.

As disclosed herein, the pre-conditioned virus exhibits improved stability characteristics as compared to the typical virus. Each of the pre-conditioned virus and the typical virus exhibits sustained stability during storage in a formulation supplemented with one or more stabilizers as compared to a formulation without the supplements. Stabilizers, used to sustain stability whether or not the virus used as the starting material for formulation after the harvest is pre-conditioned, are understood to fall broadly within three different component systems.

Single component system contains a non-viral protein or protein hydrolysate thereof as part of the formulation. The non-viral protein or protein hydrolysate serves as a stabilizer. The two component system contains a disaccharide in addition to a non-viral protein or protein hydrolysate thereof. In the two component system, both the disaccharide and the protein or the hydrolysate thereof serves as stabilizers. The three component system is similar to the two component system but has an additional disaccharide different from that in the two component system.

In our copending application No. 842/CHE/2006, we have disclosed a composition comprising a viral antigen; a first protein being selected from human serum albumin or recombinant human albumin and, a second protein, which is at least partially hydrolyzed and being selected from lactalbumin hydrolyzate, yeast hydrolyzate, peptone, and egg protein hydrolyzate and preferably and a combination of three different disaccharides wherein the virus used is being not propagated in presence of HSA. The liquid composition shows stability for 3-4 weeks at 37° C., six months at 25° C., and one year at 2° C.-8° C. while lyophilized composition shows stability for more than 50 weeks at 2° C.-8° C., 25° C., 37° C.

The liquid composition of the present invention is stable for 6 weeks at 37° C., for 6 months at 25° C. and 24 months at 2-8° C.

The lyophilized composition of the present invention is stable for 16 weeks at 37° C., for 6 months at 25° C. and 24 months at 2-8° C.

The compositions can be liquid compositions or lyophilized (dry form). The present invention discloses live attenuated rotaviruses and compositions thereof showing better and improved stability when stored at 2 to 8° C. or ambient conditions for an extended period of time. Ambient conditions can be those prevailing and typical atmospheric conditions (e.g., 25° C.) in a place but not exceeding about 37° C. The compositions of the present invention are capable of maintaining their immunizing ability during preparation and for the duration required for shelf life of a commercial vaccine (i.e., the compositions are stable).

Thus the composition of present invention exhibits stability for longer period, due to the propagation of virus in presence of human serum albumin as compared to the one being added externally.

In one example, the composition of the present invention includes a viral antigen (pre-conditioned or the typical virus), a non-viral protein or a protein that is different from the viral antigen. The term "non-viral protein" shall mean any of lactalbumin yeast protein hydrolysate, gelatin, egg protein or a vegetable protein that is corn protein, wheat protein, garbanzo bean protein, kidney bean protein, lentil protein, lima bean protein, navy bean protein, soybean protein, split pea protein and human serum albumin, all of natural or recombinant origin. Preferably, the protein is at least partially hydrolyzed. In other words, hydrolysates of these proteins or a peptone can be used in the compositions of the present invention.

The phrase "the protein is at least partially hydrolyzed", as used herein, is meant to refer to a scenario, in which the hydrolyzed protein has been at least partially been broken down into its respective amino acid building blocks. This phrase is therefore also meant to include scenarios, wherein the protein does not exist as a complete molecule anymore, but only as a collection of fragments thereof. This phrase is further meant to include a scenario wherein the protein is fully hydrolyzed. All these scenarios are also meant to be included by the phrase "protein hydrolysate," which may include a fully hydrolyzed protein, i.e. a protein broken down into its respective amino acids, or a protein partially broken down, such that a collection of peptides and amino acids exist.

Thus, the protein or the at least partially hydrolyzed version can be lactalbumin hydrolysate, yeast hydrolysate, peptone, gelatin hydrolysate, and egg protein hydrolysate or a protein from vegetable origin such as corn, wheat, garbanzo beans, kidney beans, lentils, lima beans, navy beans, soybeans, split peas or a human homologous protein such as human serum albumin which is human or recombinant origin. Such proteins and protein hydrolysates can be readily made by one skilled in the art, for example by acid hydrolysis, or can be commercially obtained. It has been shown herein that in low concentration of rotavirus, especially when the rotavirus concentration (titer) is $10^3$ FFU per 0.5 ml in the formulation, the non-viral protein such as lactalbumin hydrolysate or soy protein contribute to better and improved stability when compared to the non-viral protein—human serum albumin or bovine serum albumin. Lactalbumin hydrolysate is known to one skilled in the art and is commercially available. It is believed that lactalbumin hydrolysate provides excellent homogenization with the rota protein both in liquid form and in lyophilized form and keeps the moiety of the viral protein even when the viral protein is present in a low concentration. In place of or in addition to lactalbumin hydrolysate, others such as yeast hydrolysate, peptone, gelatin hydrolysate, and egg protein hydrolysate can also be used. The composition further includes a disaccharide or a combination of two disaccharides and a pharmaceutically acceptable buffer. The disaccharide can be any of sucrose, lactose, maltose, trehalose, cellobiose, gentobiose, melibiose, turanose and fucose. The three component system contains a combination of two different types of disaccharides in addition to a non-viral protein or protein hydrolysate thereof. Those proteins or protein hydrolysates and disaccharides in this paragraph are referred to herein as "stabilizers."

The stabilizers can be added to an excipient, diluent or carrier (e.g., a pharmaceutically acceptable buffer) that is routinely used in pharmaceutical formulations of the virus. Such excipients or carriers are well known in the art. Specifically, a suitable diluent or a pharmaceutically acceptable buffer is supplemented with one or more above-referenced stabilizers. In a preferred embodiment, to the rotavirus containing sample LAH is first added, followed by sucrose. If a second disaccharide is added, then trehalose is preferred next in the sequence. The composition without the stabilizers is essentially a carrier solution or pharmaceutically acceptable buffer. In addition to the named stabilizers, the composition can contain colors, flavors, sweeteners, adsorbents and/or flow promoters. Preferably, these compositions are buffered at an appropriate pH, usually between 6 and 8, preferably between 6.8 and 8.0. For example, in one embodiment, the composition according to the present invention may be formulated in Dulbecco's Modified Eagles medium.

In one aspect, the present invention discloses a formulation containing a live attenuated and pre-conditioned rotavirus population. The pre-conditioned rotavirus exhibits a certain level stability in a pharmaceutically acceptable excipient without any supplemental stabilizers in the composition. The stability of the pre-conditioned rotavirus population is better when compared to a live attenuated typical rotavirus population that is not so pre-conditioned. The typical rotavirus population, in terms of its stability characteristics, shows a loss of log 4 titer whereas the pre-conditioned virus shows a loss significantly less than log 4 titer loss, when both stored at 37° C. for four weeks after harvest.

In another aspect, the present invention discloses a composition containing a live attenuated pre-conditioned rotavirus that is capable of exhibiting a minimum of 0.8 log to a maximum of 1.1 logs per ml enhanced titer as compared to the live attenuated typical rotavirus when stored at ambient conditions without any supplemental stabilizers in the composition.

In either case, the stability of the pre-conditioned virus can be improved if at least one stabilizer such as lactalbumin hydrolysate, yeast hydrolysate, gelatin hydrolysate, and egg protein hydrolysate, peptone, a vegetable protein and a human serum albumin is added to the composition. The improved stability can be further improved by adding a disaccharide or a combination of different disaccharides to the composition. Thus, in a most preferred embodiment a composition contains a viral antigen that is a pre-conditioned rotavirus, a protein different from said viral antigen, at least partially hydrolyzed (such as, for example, lactalbumin, yeast protein, peptone, gelatin, and egg protein, corn protein, wheat protein, garbanzo bean, kidney bean, lentil, lima bean, navy bean, soybeans, split peas or human serum albumin isolated from human or recombinant human serum albumin and a disaccharide or a combination of two disaccharides. A composition with a typical virus is also preferred when stabilizers are present in the composition as better stability of the typical virus can be achieved in such a composition as compared to the typical virus in a composition without these stabilizers.

The proteins, either alone or in the combination of two proteins, can be present in the range of 0.01% (w/v) to 80% (w/v), preferably in the range from 0.05% to 50%. Preferably, the protein used as a stabilizer is any of lactalbumin hydrolysate, human serum albumin and soy protein. Lactalbumin hydrolysate can be present in the composition at about 0.01% to 70%, preferably 0.1% to 30%. Soy protein can be present in the composition at about 0.01% to 70%, preferably 0.05% to 20%. The human serum albumin is preferably of recombinant origin and can be present in the composition at about 0.01% to 20%, preferably 0.1% to 0.5%.

Preferably, the disaccharide used as a stabilizer can be any of trehalose, lactose and sucrose. Preferred trehalose concentration is at about 0.01% to 70%, most preferably 0.5% to 20%. The combination of two different disaccharides can be any two of sucrose, lactose, maltose, trehalose, cellobiose, gentobiose, melibiose and turanose. For example, the combination of two disaccharides can be any of sucrose and maltose, sucrose and lactose, sucrose and trehalose, maltose and trehalose or trehalose and lactose. Preferred combination of disaccharides is sucrose and trehalose. Preferably, sucrose is present at about 1-10% and 70% (w/v) to 85% (w/v), more preferably at 5% to 10% and 80% to 85% (w/v) and trehalose is present at about 0.01% (w/v) to 50.0% (w/v), preferably 0.5% to 20% (w/v). The combined or a single disaccharide concentration can be about 1-10% or about 20%-85% (w/v). In an embodiment, the concentration of the disaccharides can be as follows: sucrose about, 1-10% and 70% to 85% (w/v), preferably 5 to 10% or 80% to 85% (w/v), lactose about 0.1% to 20.0% (w/v), preferably 0.5% to 10% (w/v), maltose about 0.1% (w/v) to 50% (w/v), preferably 5% to 50% (w/v), trehalose about 0.01% (w/v) to 70.0% (w/v) preferably 0.5% to 20.0% (w/v).

Preferably, the composition is buffered, using a phosphate-citrate buffer. Preferably, the phosphate-citrate buffer is approximately 310 mM phosphate and approximately 100 mM citrate. Pharmaceutically acceptable buffer can have a pH value in the range from 6.8 to 8.0. The buffer can be any of phosphates, carbonates, citrates, Tris, HEPES buffers as well as combinations thereof. The phosphate can have a concentration in the range from 10 mM to 1000 mM, preferably from 50 mM to 310 mM. The carbonate can have a concentration in the range from 10 mM to 1000 mM, preferably from 50 mM to 300 mM. The citrate can have a concentration in the range of from 10 mM to 400 mM, preferably from 50 mM to 100 mM. The Tris can have a concentration in the range of from 0.1 mM to 1000 mM, preferably from 5 mM to 20 mM. The HEPES can have a concentration in the range of from 0.1 mM to 1000 mM, preferably from 10 mM to 20 mM.

In some embodiments starch can also be used as a stabilizer. Examples of starch are corn, wheat, maize and rice. The starch can be any of soluble, insoluble, partly or fully hydrolyzed starches. The starch is can be present at about 0.01% to 10%, preferably 0.1% to 3.0%.

The composition can contain at least one diluent such as tissue culture medium, normal saline, phosphate buffered saline or water. The preferred diluent is Dulbecco's Modified Eagles Medium (DMEM). The composition can further contain at least one chemical such as ascorbic acid, gum arabic, gum acacia, polyvinyl pyrollidine, pyridoxine HCl (Vitamin B 6) and the concentration can be at about 0.1% to 20%, preferably 0.25% to 5% by weight of the composition. The composition is preferably a liquid formulation with live attenuated rotavirus. Preferred liquid formulation contains a pre-conditioned or a typical rotavirus and stabilizers, lactalbumin hydrolysate (LAH) ranging from 20-30% w/v and trehalose at about 0.5% w/v. Another preferred liquid formulation contains a pre-conditioned or a typical rotavirus and stabilizers, lactalbumin hydrolysate in the composition at about 5% w/v, sucrose at about 80% w/v and trehalose at about 0.5% w/v. The compositions according to the present invention can be used as a vaccine for vaccination against virus infection and virus associated diseases. The rotavirus strains 116E (G9P[11]) and I321 (G10P[11]) are natural human-bovine reassortant, naturally attenuated and confer substantial level of immunity in infants and young children. While the human rotavirus is a preferred, other rotaviruses that can be formulated according to the present invention are bovine rotavirus, porcine rotavirus and human-bovine reassortant rota viruses, lamb rotavirus, sheep rotavirus. Suitable compositions and formulations as disclosed herein are required to keep the stability of low titer rotavirus, i.e., $10^3$ sustained given that it is known to be a challenging task to keep the stability of the low parent titer values sustained during storage. A rotavirus vaccine that exhibits an improved and/or sustained stability can be used for the prevention of a virus infection, preferably a rotavirus infection and/or rotavirus gastroenteritis in children worldwide. Preferably, the treatment or prevention involves administering three oral doses of an effective amount of the composition to an infant within 8-20 weeks of age at the time of dose 1.

The following table (Table 1) gives the comparison between formulations of typical Rotavirus i.e. propagated in absence of human serum albumin (1 to 8) and in presence of human serum albumin (1A to 8A) and clearly shows that the formulations comprising virus propagated in presence of human serum albumin exhibit more stability.

TABLE 1

| S. No | Log Loss at 37 deg C. | Time point | Log Loss at 25 deg C. | Time point |
|---|---|---|---|---|
| 1 | 5 | 4 wks | 1.19 | 24 wks |
| 1A | 3.73 | 12 wks | 0.91 | 24 wks |
| 2 | 4 | 4 wks | 1.09 | 24 wks |
| 2A | 3.63 | 20 wks | 0.76 | 24 wks |
| 3 | 4.45 | 3 wks | 3.48 | 16 wks |
| 3A | 3.3 | 12 wks | 2.21 | 24 wks |
| 4 | 4.43 | 4 wks | 1.9 | 20 wks |
| 4A | 3.72 | 12 wks | 1.61 | 24 wks |
| 5 | 4.96 | 4 wks | 1.66 | 24 wks |
| 5A | 3.39 | 8 wks | 1.08 | 24 wks |
| 6 | 4.77 | 8 wks | 0.86 | 24 wks |
| 6A | 3.32 | 12 wks | 0.39 | 24 wks |
| 7 | 5.39 | 4 wks | 1.98 | 24 wks |
| 7A | 2.44 | 12 wks | 0.28 | 24 wks |
| 8 | 4.46 | 4 wks | 1.96 | 24 wks |
| 8A | 3.1 | 20 wks | 0.34 | 24 wks |

The present study also provides a method for adapting rotavirus, e.g. natural human-bovine reassortants, naturally attenuated rotavirus strains 116E (G9P[11]) and I321 (G10P [11]) to suitable cells, e.g. Vero cells. In one embodiment, adapting involves serial passages, 2-20 passages, preferably 2-5 passages. Preferably, each passage occurs over a time period in the range of from 24 hours to generally 6 days and maximum of 10 days. Preferably, the virus is human rotavirus. The method includes optimized dose of trypsin (0.1 μg/ml to 30 μg/ml) and/or calcium chloride (100 μg/ml to 1000 μg/ml) for viral activation and virus maintenance medium where high titer ($10^4$ to $10^8$ FFU/ml) of virus harvest is within 48 hrs to six days. Also use of the adapted strains for making stable, live, monovalent, liquid rotavirus vaccine composition is envisaged. The present invention further discloses how to produce typical and pre-conditioned rotaviruses. Furthermore, the present invention provides for the use of a viral antigen, protein, a combination of one or two different disaccharides for the manufacture of a composition according to the present invention for the treatment or prevention of virus associated diseases, preferably rotavirus associated diseases.

WORKING EXAMPLES

The following working examples are provided to demonstrate preferred embodiments of the invention, but of course, should not be construed as in any way limiting the scope of the present invention. The examples below were carried out using conventional techniques that are well known and routine to those of skill in the art, except where otherwise described in detail. Further, it should be appreciated by those of skill in the art that the techniques disclosed in the examples represent techniques found by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Production of Typical and Pre-conditioned Rotavirus Populations in Bulk and Their Stability Characteristics Bharat Biotech International Ltd (BBIL) obtained the human rotavirus strains, 116E and I321 from National Institute of Health (NIH) under the material transfer agreement with National Institute of Allergy and Infectious Diseases (NIAID), NIH, Bethesda, USA. The original 116E (G9[P11]) and I321 (G10P[11]) were adapted to grow in cell culture by passages in primary African Green Monkey Kidney (AGMK) cells, then in MA104 cell substrate and later in Serially Passaged AGMK (SPAGMK) cells. MA104 and SPAGMK cell substrates are not approved by National Regulatory Authorities (NRA) for use in commercial vaccine production. Hence the two human rotavirus vaccine strains (116E and I321) were adapted to Vero cells, grown separately in these cells to produce viral bulk populations and individually prepared as pilot lots of monovalent, live, attenuated, oral rotavirus vaccine liquid formulations for human clinical trials. The human rotavirus strain 116E, a natural human-bovine reassortant and naturally attenuated, is a human G9 strain into which a single bovine VP4 gene (VP=viral protein), homologous to the P[11] gene segment, was naturally introduced. The I321 strain, named G10P [11], is primarily composed of bovine genes and has only two gene segments of human origin, VP5 and VP7. The specific examples herein have been described with reference to the live and attenuated strain 116E.

In general, the production process was as follows: Working Cell Banks of Vero cells were used to grow rotaviruses. The Vero cells were propagated in Dulbecco's Modified Eagles Medium (DMEM) (Sigma®, MO, USA) with 5-10% of fetal bovine serum. Rotaviruses require a tryptic cleavage of one of the two major outer coat proteins VP4 in the presence of calcium chloride to capably infect Vero cells in vitro. Rotavirus strains were made into the seed lot system of Master Virus Bank and Working Virus Bank. Vero cells in serum free medium were infected with the chosen strain and single harvests were made after every 48 hours for the duration of 144 hours. Three single harvests were pooled as one bulk and a sucrose phosphate glutamate stabilizer was added. Such pooled bulks were stored at −70° C. or 2-8° C. Two methods of manufacturing bioprocess were followed to produce the bulk live attenuated viral population.

Typical virus production: Working Cell Bank of Vero cells stored in liquid nitrogen were used for the revival and growth of Vero Cell monolayers for the production process. Two cryovials of Working Cell Bank were thawed out carefully from the liquid nitrogen storage container and transferred the cells into two T-150 polystyrene sterile culture flasks for revival and supplemented with DMEM containing 5% of fetal bovine serum. The culture flasks were incubated at 37° C. for twenty-four hours. After the incubation period, the medium was decanted from the cultures and replenished with DMEM containing 5% of fetal bovine serum medium to promote formation of confluent monolayers.

The culture flasks were observed under the microscope for their morphology and ability to expand in the medium used. The cells were further propagated to two more passages to obtain several containers of cells for infection with rotavirus 116E or I321.

Rotavirus 116E or I321 was selected from the Working Virus Bank of the seed lot system and was trypsin-activated and inoculated to infect the cells. The calculation of multiplicity of infection was done according to the population of cells. The cells were infected and were kept at 37° C. for one hour for adsorption. After the adsorption time, the cell cultures were topped up with DMEM without serum. The infected cell cultures were maintained at 35° C., and single harvests were collected after every 48 hours for the duration of 144 hours. After every single harvest the cell cultures were replenished with DMEM without serum. The cell cultures were terminated after the third single harvest. The filtered single harvests were collected in sterile containers and stored at 2-8° C. The single harvests were pooled to form the pooled bulk and kept at 2-8° C. Sampling was done to test for virus content, sterility for every single harvest and the pooled bulk. The pooled bulk was stored at −70° C. or 2-8° C. in SPG stabilizer (sucrose 7.46%, Potassium dihydrogen phosphate 0.0515%, di-Potassium hydrogen phosphate 0.128% and Glutamate 0.101%). Aliquots of samples were also taken from the single harvests without stabilizers for obtaining stability data at different temperatures.

Pre-conditioned virus production: Working Cell Bank of Vero cells stored in liquid nitrogen were used for the revival and growth of Vero Cell monolayers for the production process. Two cryovials of Working Cell Bank were thawed out carefully from the liquid nitrogen storage container and transferred the cells into two T-150 polystyrene sterile culture flasks for revival and supplemented with DMEM containing 5% fetal bovine serum and 0.1% human serum albumin. The culture flasks were incubated at 37° C. for twentyfour hours. After the incubation period, the medium was decanted from the culture flasks and replenished with DMEM containing 5% fetal bovine serum and 0.1% human serum albumin to promote formation of confluent monolayers.

A second set of cell cultures have been set each with 0.1%, 0.2%, 0.3%, 0.5% or 1% human serum albumin (of human origin) along with 5% Fetal bovine serum in DMEM. A third set of cell cultures have also been set up each with 0.1%, 0.2%, 0.3%, 0.5% or 1% human serum albumin (recombinant origin) along with 5% fetal bovine serum in DMEM.

Rotavirus 116 E or I321 cryovial was selected from the Working Virus Bank of the seed lot system and inoculums were prepared to infect the Vero cell cultures. The determination of multiplicity of infection was done according to the population of the cells. The cell cultures were washed twice with phosphate buffer saline pH 7.4 to 7.6. The cell cultures were infected and were kept at 37° C. for one hour for adsorption of virus. After the adsorption time, the cell cultures were topped up with DMEM with 0.1% of human serum albumin. Human origin or recombinant human serum albumin was added to the cell cultures. The infected cell cultures were maintained at 37° C., and multiple harvests were collected after every 48 hours and the cultures are replenished with their respective human serum albumin (human origin and recombinant human serum albumin) containing medium. The harvests were collected in sterile containers. Harvests were stored at 2-8° C. The infected cultures were kept at 37° C. for the virus multiplication and maintenance of the cells till third harvest and the cultures were terminated after their third harvest. The three harvests from each set was pooled to form the pooled bulk and kept at 2-8° C. Sampling was done to test for virus content and sterility for every single harvest pooled bulks. The pooled bulk was stored at −70° C. or 2-8° C. in SPG stabilizer (sucrose 7.46%, Potassium dihydrogen phosphate 0.0515%, di-Potassium hydrogen phosphate 0.128% and Glutamate 0.101%). Aliquots were collected from the single harvests without stabilizers for obtaining stability data at different temperatures.

Shown in FIG. 1 is the average titer data obtained from the typical virus and pre-conditioned virus in five experiments. All the five experiments were performed with the same parameters to demonstrate that the presence of HSA in the culture medium during the multiplication of the rotavirus on Vero cell substrate does result in a higher titer than without HSA. Three single harvests on $2^{nd}$, $4^{th}$ and $6^{th}$ day after infection were collected and pooled; the titer was the average for the 3 harvests at 2°-8° C. The pre-conditioned virus exhibited higher titer yield. The average titer showed the minimum titer difference of 0.8 logs and the maximum of 1.1 logs per ml.

Example 2

Formulation of the Typical and Pre-conditioned Rotaviruses in Liquid and Lyophilized Forms and the Effect of Each Formulation on Stability Characteristics The pooled bulks, stored at 2-8° C. or −70° C., were formulated into Final Bulks based on the targeted titer $10^3$ to $10^{8.5}$ FFU/0.5 mL and filled as vaccine. Based on the titer of the pooled bulk, a calculated volume of the pooled bulk was taken and added to a predetermined volume of Final Bulk that contained stabilizers, antibiotics and buffers. The formulated Final Bulk was filled as vaccine into vials. The various stabilizers used in different combinations and concentrations in the formulations were lactalbumin hydrolysate (LAH), trehalose, sucrose, starch, lactose, maltose, soy protein, rHSA (not including any residual rHSA that might have been carried over with the pre-conditioned virus harvested from the pre-conditioned virus production process). 0.5 ml aliquots of the virus containing formulation was aseptically transferred to 2.0 ml vial and stored at 2-8° C., 25° C. and 37° C. Stability parameters were tested at periodic intervals to demonstrate the stability of the typical virus and pre-conditioned virus after formulation with various stabilizers (see Table 2).

Preparation of liquid formulations 1-25: Various formulations were prepared by calculating the volume of stabilizers, buffer and volume of the viral antigen and the target titre under aseptic conditions. Sampling from each formulation was done aseptically and labeled individually to indicate the sample number, date of preparation and sample meant for particular temperature storage. Sample vials were stored at 2°-8° C., 25° C. and 37° C. Sample numbers are coded and tested for their titres periodically as per the stability study plan. The results were represented in the Figures from FIG. 1 to FIG. 12.

Preparation of lyophilized formulations 26-45: Various formulations prepared by calculating the volume of stabilizers, buffer and volume of the viral antigen and the target titre under aseptic conditions. Formulated Final Bulks are filled in freeze drying vials aseptically and they are subjected for 42 hrs to 48 hrs freeze drying process. The freeze drying process normally had three segments: pre cooling, primary drying and secondary drying. The freeze drying cycle was set to favor the eutectic points of various stabilizers used in different formulations. Once the freeze drying was completed, the vials were properly sealed under vacuum. Sampling from each formulation was done aseptically and labeled individually to indicate the sample number, date of preparation and sample meant for particular temperature storage. Sample vials were stored at 2°-8° C., 25° C. and 37° C. Samples were tested for their titres periodically as per the stability study plan. The lyophilized vials were reconstituted using WF1.

TABLE 2

| | Stabilizer | | | | | | | | | | | |
|---|---|---|---|---|---|---|---|---|---|---|---|---|
| F. No. (FIG) | LAH | Suc | Treh | Star | Lact | Malt | Soy | HSA | PVP | bicarb mM | Gum | Pyr HCL |
| 1 (2B) | 5.0 | 80.0 | 0.5 | 0.0 | 0.0 | 0.0 | 0.0 | 0.0 | 0.0 | 0.0 | 0.0 | 0.0 |
| 2 (3) | 2.5 | 0.0 | 0.0 | 0.0 | 0.0 | 0.0 | 0.0 | 0.0 | 0.0 | 0.0 | 0.0 | 0.0 |
| 3 (3) | 10.0 | 0.0 | 0.5 | 0.0 | 0.0 | 0.0 | 0.0 | 0.0 | 0.0 | 0.0 | 0.0 | 0.0 |
| 4 (3) | 20.0 | 0.0 | 0.0 | 0.0 | 0.0 | 0.0 | 0.0 | 0.0 | 0.0 | 0.0 | 0.0 | 0.0 |
| 5 (3) | 2.5 | 0.0 | 0.5 | 0.5 | 0.0 | 0.0 | 0.0 | 0.0 | 0.0 | 0.0 | 0.0 | 0.0 |
| 6 (4) | 5.0 | 80 | 0.5 | 0.0 | 0.0 | 0.0 | 0.0 | 0.0 | 0.0 | 0.0 | 0.0 | 0.0 |
| 7 (5) | 20.0 | 0.0 | 0.5 | 0.0 | 0.0 | 0.0 | 0.0 | 0.0 | 0.0 | 0.0 | 0.0 | 0.0 |
| 8 (5) | 10.0 | 0.0 | 0.0 | 0.0 | 1.0 | 0.0 | 0.0 | 0.0 | 0.0 | 0.0 | 0.0 | 0.0 |
| 9 (5) | 5.0 | 80 | 0.0 | 0.0 | 0.0 | 0.0 | 0.0 | 0.0 | 0.0 | 0.0 | 0.0 | 0.0 |
| 10 (5) | 10.0 | 0.0 | 0.0 | 0.0 | 0.0 | 50 | 0.0 | 0.0 | 0.0 | 0.0 | 0.0 | 0.0 |
| 11 (6) | 0.5 | 0.0 | 1.0 | 0.0 | 0.0 | 0.0 | 10.0 | 0.0 | 0.0 | 0.0 | 0.0 | 0.0 |
| 12 (6) | 0.5 | 0.0 | 0.0 | 0.0 | 1.0 | 0.0 | 10.0 | 0.0 | 0.0 | 0.0 | 0.0 | 0.0 |
| 13 (6) | 5.0 | 80.0 | 0.0 | 0.0 | 0.0 | 0.0 | 2.5 | 0.0 | 0.0 | 0.0 | 0.0 | 0.0 |
| 14 (6) | 5.0 | 0.0 | 0.0 | 0.0 | 0.0 | 50.0 | 2.5 | 0.0 | 0.0 | 0.0 | 0.0 | 0.0 |
| 15 (7) | 10.0 | 10 | 1.0 | 0.0 | 0.0 | 0.0 | 0.0 | 0.0 | 0.0 | 0.0 | 0.0 | 0.0 |
| 16 (7) | 10.0 | 0.0 | 1.0 | 0.0 | 0.0 | 5.0 | 0.0 | 0.0 | 0.0 | 0.0 | 0.0 | 0.0 |
| 17 (7) | 2.5 | 80 | 1.0 | 0.0 | 0.0 | 0.0 | 0.0 | 0.0 | 0.0 | 0.0 | 0.0 | 0.0 |
| 18 (7) | 2.5 | 0.0 | 1.0 | 0.0 | 0.0 | 50.0 | 0.0 | 0.0 | 0.0 | 0.0 | 0.0 | 0.0 |
| 19 (8) | 5.0 | 80.0 | 0.5 | 0.0 | 0.0 | 0.0 | 0.0 | 0.0 | 0.0 | 0.0 | 0.0 | 0.0 |
| 20 (8) | 5.0 | 80.0 | 0.5 | 0.0 | 0.0 | 0.0 | 0.0 | 0.0 | 0.0 | 0.0 | 0.0 | 0.0 |
| 21 (8) | 0.0 | 80 | 0.5 | 0.0 | 0.0 | 0.0 | 0.0 | 0.1 | 0.0 | 0.0 | 0.0 | 0.0 |
| 22 (8) | 0.0 | 80 | 0.5 | 0.0 | 0.0 | 0.0 | 0.0 | 0.1 | 0.0 | 0.0 | 0.0 | 0.0 |
| 23 (8) | 0.0 | 80 | 0.5 | 0.0 | 0.0 | 0.0 | 0.0 | 0.0 | 0.0 | 0.0 | 0.0 | 0.0 |
| 24 (8) | 0.0 | 80 | 0.5 | 0.0 | 0.0 | 0.0 | 0.0 | 0.0 | 0.0 | 0.0 | 0.0 | 0.0 |
| 25 (2A 9&10) | 0.0 | 0.0 | 0.0 | 0.0 | 0.0 | 0.0 | 0.0 | 0.0 | 0.0 | 0.0 | 0.0 | 0.0 |
| 26 (13) | 0.0 | 12.0 | 0.0 | 0.0 | 0.0 | 0.0 | 0.0 | 0.5 | 0.0 | 0.0 | 0.0 | 0.0 |
| 27 (13) | 0.5 | 0.0 | 0.5 | 0.0 | 0.0 | 0.0 | 0.0 | 0.0 | 0.0 | 0.0 | 0.0 | 0.0 |
| 28 (13) | 0.0 | 0.0 | 0.5 | 0.0 | 0.0 | 0.0 | 0.5 | 0.0 | 0.0 | 0.0 | 0.0 | 0.0 |
| 29 (13) | 0.0 | 0.0 | 0.5 | 0.0 | 0.0 | 0.0 | 0.0 | 0.0 | 0.25 | 0.0 | 0.0 | 0.0 |
| 30 (14) | 0.0 | 12.0 | | 0.1 | 0.0 | 0.0 | 0.0 | 0.5 | 0.0 | 0.0 | 0.0 | 0.0 |
| 31 (14) | 0.5 | 0.0 | 0.5 | 0.1 | 0.0 | 0.0 | 0.0 | 0.0 | 0.0 | 0.0 | 0.0 | 0.0 |
| 32 (14) | 0.0 | 0.0 | 0.5 | 0.1 | 0.0 | 0.0 | 0.5 | 0.0 | 0.0 | 0.0 | 0.0 | 0.0 |
| 33 (14) | 0.0 | 0.0 | 0.5 | 0.1 | 0.0 | 0.0 | 0.0 | 0.0 | 0.25 | 0.0 | 0.0 | 0.0 |
| 34 (15) | 0.0 | 12.0 | 0.0 | 0.1 | 0.0 | 0.0 | 0.0 | 0.5 | 0.0 | 304 | 0.0 | 0.0 |
| 35 (15) | 0.5 | 0.0 | 0.5 | 0.1 | 0.0 | 0.0 | 0.0 | 0.0 | 0.0 | 304 | 0.0 | 0.0 |
| 36 (15) | 0.0 | 0.0 | 0.5 | 0.1 | 0.0 | 0.0 | 0.5 | 0.0 | 0.0 | 304 | 0.0 | 0.0 |
| 37 (15) | 0.0 | 0.0 | 0.5 | 0.1 | 0.0 | 0.0 | 0.0 | 0.0 | 0.25 | 304 | 0.0 | 0.0 |
| 38 (16) | 0.0 | 12 | 0.0 | 0.0 | 0.0 | 0.0 | 0.0 | 0.5 | 0.0 | 0.0 | 0.1 | 0.0 |
| 39 (16) | 0.5 | 0.0 | 0.5 | 0.0 | 0.0 | 0.0 | 0.0 | 0.0 | 0.0 | 0.0 | 0.1 | 0.0 |
| 40 (16) | 0.0 | 0.0 | 0.5 | 0.0 | 0.0 | 0.0 | 0.5 | 0.0 | 0.0 | 0.0 | 0.1 | 0.0 |
| 41 (16) | 0.0 | 0.0 | 0.5 | 0.0 | 0.0 | 0.0 | 0.0 | 0.0 | 0.25 | 0.0 | 0.1 | 0.0 |
| 42 (17) | 0.5 | 0.0 | 0.0 | 0.0 | 0.0 | 0.0 | 0.0 | 0.0 | 0.25 | 0.0 | 0.0 | 0.0 |
| 43 (17) | 0.5 | 0.0 | 0.0 | 0.0 | 0.0 | 0.0 | 0.0 | 0.0 | 0.0 | 0.0 | 0.1 | 0.0 |
| 44 (17) | 0.5 | 0.0 | 0.0 | 0.0 | 0.0 | 0.0 | 0.0 | 0.0 | 0.0 | 0.0 | 0.0 | 0.1 |
| 45 (17) | 0.5 | 0.0 | 0.0 | 0.1 | 0.0 | 0.0 | 0.0 | 0.0 | 0.0 | 0.0 | 0.0 | 0.0 |

Figure 2A:
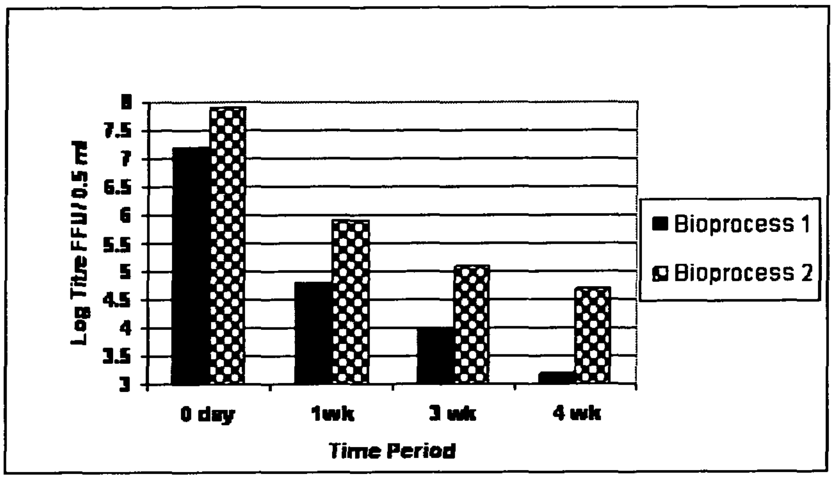
Figure 2B:
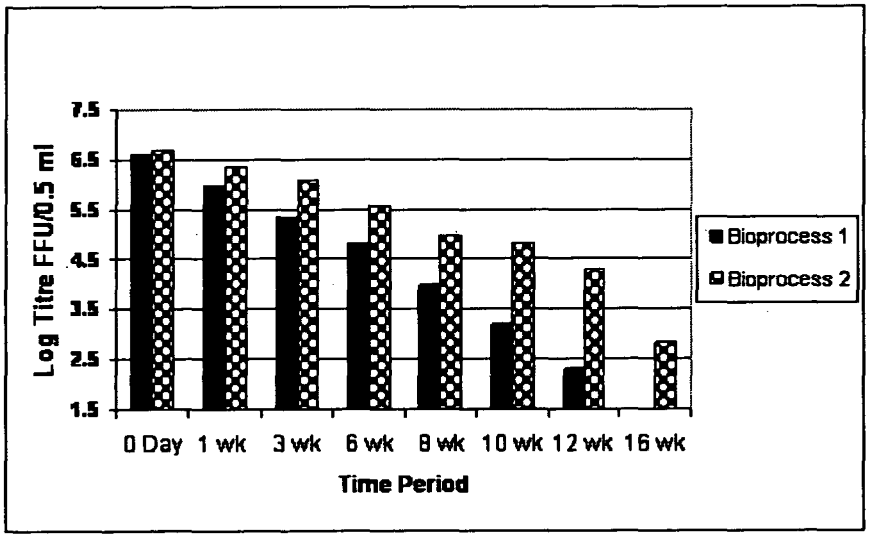

*Abbreviations and Explanations:
F. No.—Formulation Number
PVP—Polyvinyl pyrrolidone
Bicarb—304 mM bicarbonate
Gum—Gum Acasia
Pyr HCL—Pyridoxine HCL
Formulations 1-24 are liquid formulations with stabilizers
Formulations 19, 20, 23 and 24 use the typical virus
Formulations 21 and 22 use the pre-conditioned virus
Formulation 25—liquid formulation with only buffer without stabilizers
Formulations 26-45 are lyophilized formulations Shown in FIG. 2 is stability data for the typical virus and pre-conditioned virus in the absence (2A) or presence (2B) of stabilizers 5% LAH+80% sucrose+0.5% trehalose in the liquid formulation (F. No. 1) stored at 37° C. At this temperature, the viral stability is seen to drop gradually starting with 0 day to $16^{th}$ week with or without stabilizers. In the absence of the stabilizers, the drop in pre-conditioned viral titer is 3.2 logs after 4 weeks at 37° C. whereas the drop in typical viral titer is 4.0 logs. As can be noted from FIG. 2B, the presence of stabilizers did delay the drop in titer to the levels seen in the absence of the stabilizers. Further, with or without stabilizers, the reduction in titer is little slower in the case of the pre-conditioned is than the typical virus demonstrating that the HSA used in the production process did contribute materially to the stability.

Figure 3A:
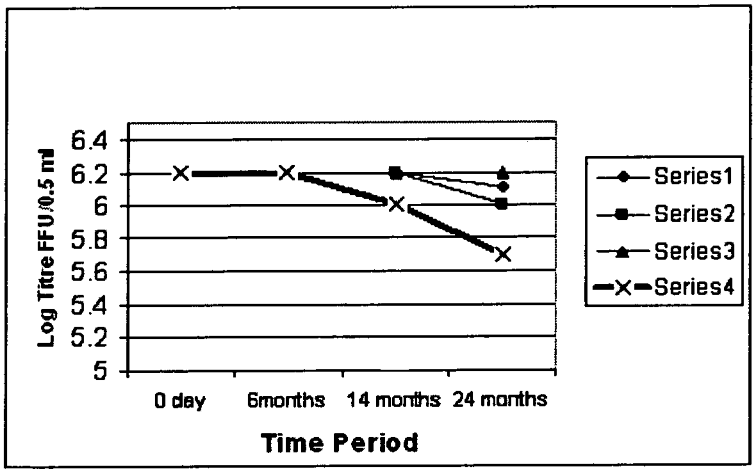
Figure 3B:
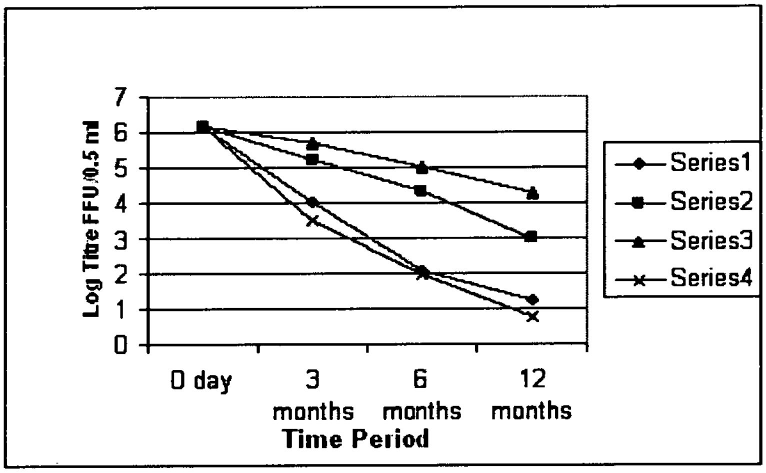
Figure 3C:
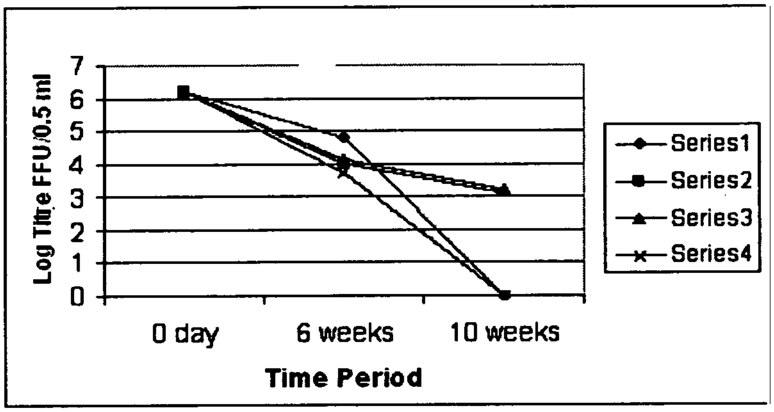

Shown in FIG. 3 is the stability data for the rotavirus in four different formulations at 2-8° C. (3A), 25° C. (3B) and 37° C. (3C). In each case, series 1 refers to a formulation with 2.5% lactalbumin hydrolysate, series 2 refers to a formulation with 10% lactalbumin hydrolysate, and 0.5% trehalose, series 3 refers to a formulation with 20% lactalbumin hydrolysate and series 4 refers to a formulation with the combination of 2.5% lactalbumin hydrolysate, 0.5% of Starch and 0.5% of trehalose. At 2-8° C., there was no titer drop in series 3 after up to twenty four months, and 0.09 log to 0.49 logs titer drop was observed in series 1, 2 & 4 after 14 months to 24 months at 2-8° C. At 25° C., series 1 to 4 showed a titer drop in the range of 0.94 logs to 2.69 logs after 3 months and in the range of 1.19 to 4.19 logs after 6 months and in the range of 1.89 to 5.39 after 12 months. At 37° C., series 1 to 4 showed the drop in titer at the range of 1.39 to 2.49 logs after six weeks and series 2 and 3 showed a titer drop of 2.99 to 3.09 logs after 10 weeks. In series 1 and 4, the titer became nil after ten weeks.

Figure 4A:
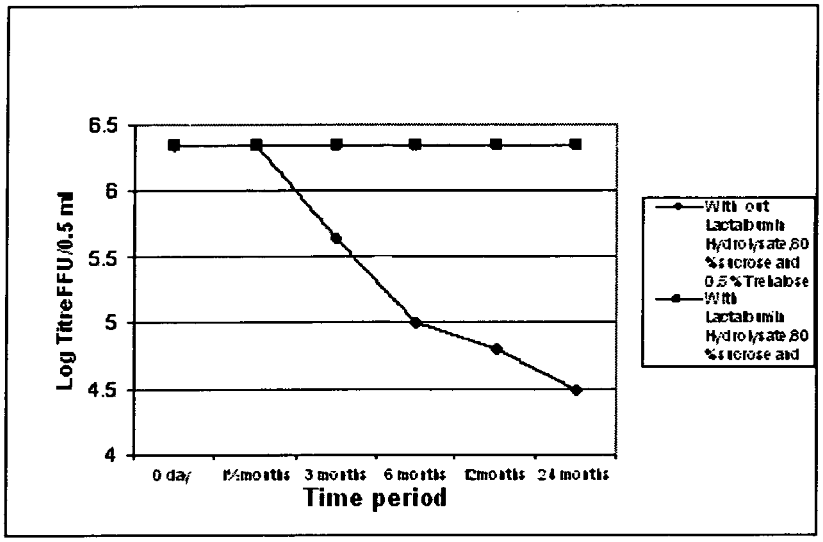
Figure 4B:
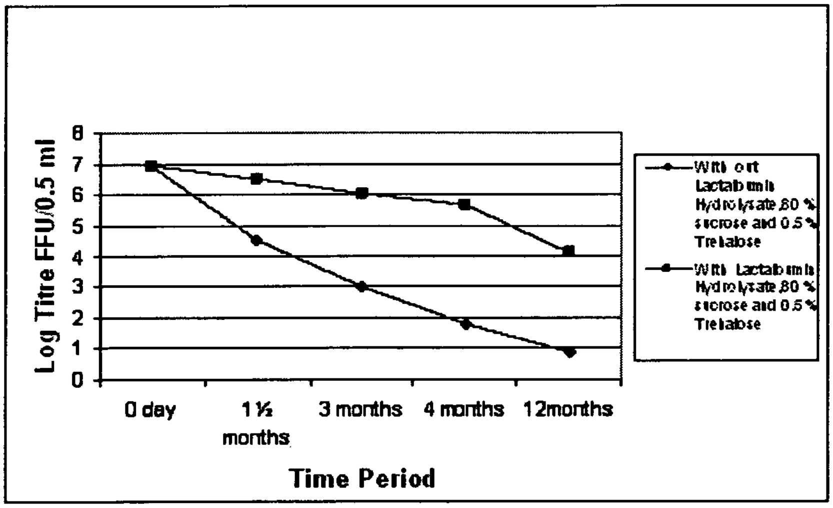
Figure 4C:
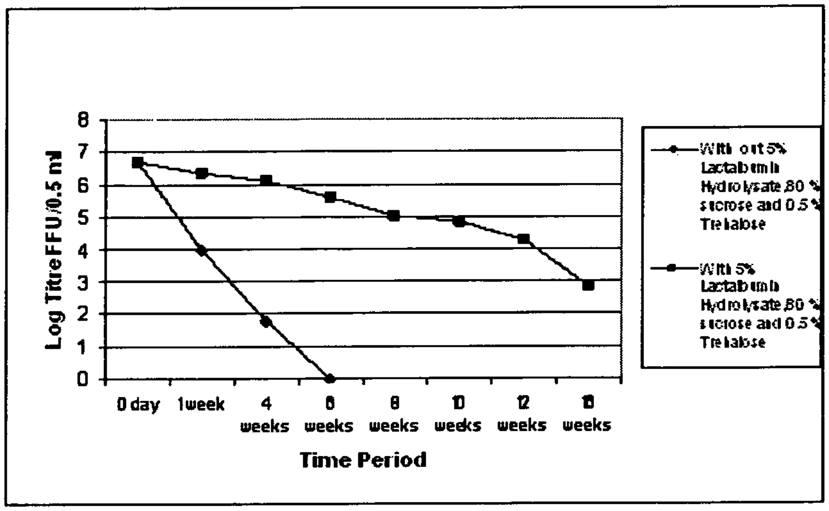

Shown in FIG. 4 is the stability data for the rotavirus 116 E in a formulation with or without stabilizers—5% lactalbumin hydrolysate+80% sucrose+0.5% trehalose—kept at 2-8° C. (4A), 25° C. (4B) and 37° C. (4C). At 2-8° C., the rotavirus formulation without lactalbumin hydrolysate and the two disaccharides showed gradual titer loss of 1.84 logs up to the period of 24 months. Rotavirus with 5% lactalbumin hydrolysate and the combination of 80% sucrose and 0.5% trehalose showed no drop in titer up to the period of 24 months. At 25° C., the rotavirus formulation without lactalbumin hydrolysate and a combination of two disaccharides showed titer loss of 6.0 logs up to the period of 12 months. Rotavirus with 5% lactalbumin hydrolysate and a combination of 80% sucrose and 0.5% trehalose showed gradual drop of 2.81 logs in titer up to the period of 12 months. At 37° C., the rotavirus formulation without lactalbumin hydrolysate and a combination two disaccharides showed total titer loss after 6 weeks. Rotavirus with 5% lactalbumin hydrolysate and a combination of 80% sucrose and 0.5% trehalose showed gradual drop of 3.85 logs in titer up to the period of 16 weeks.

Figure 5A:
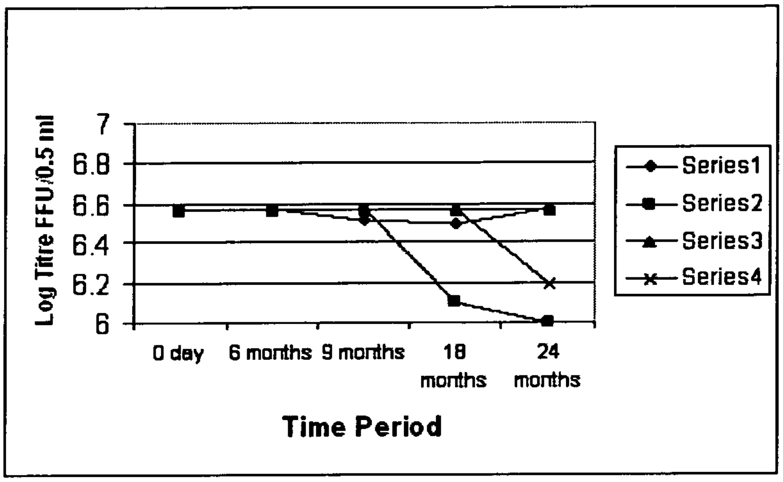
Figure 5B:
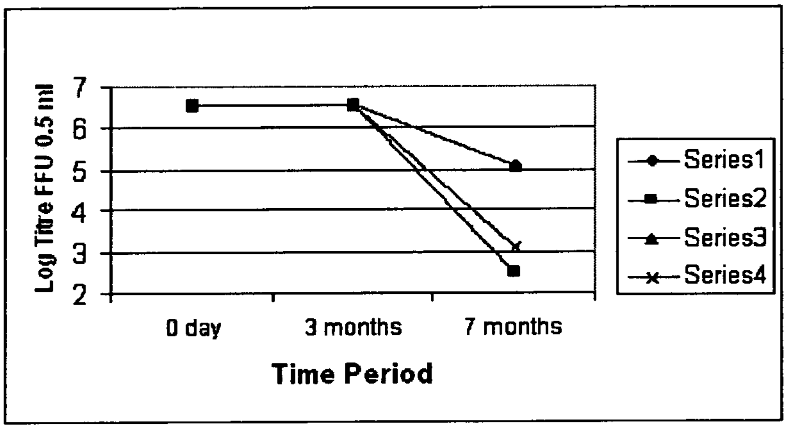
Figure 5C:
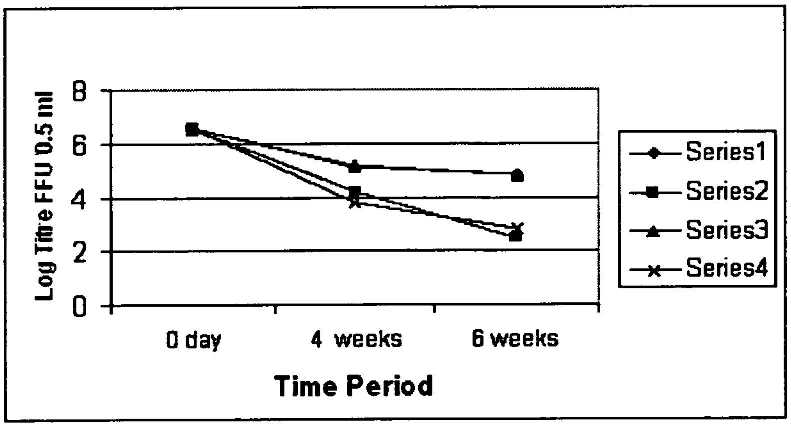

Shown in FIG. 5 is the stability data for the rotavirus in four different formulations at 2-8° C. (5A), 25° C. (5B) and 37° C. (5C). In each case, series 1 refers to a formulation with the combination of 20% lactalbumin hydrolysate, and 0.5% of trehalose, series 2 refers to a formulation with the combination of 10% lactalbumin hydrolysate, 1.0% of lactose, series 3 refers to a formulation with the combination of 5% lactalbumin hydrolysate, 80% of sucrose and series 4 refers to a formulation with the combination of 10% lactalbumin hydrolysate and 50% of maltose. At 2-8° C., the titer did not drop in series 1 and 3 up to 24 months and 2 and 4 series showed no titer drop till nine months and 0.37 to 0.57 logs drop was observed after 24 months. At 25° C., there was no titer drop in all four series up to three months at 25° C. and 1.47 logs loss after 7 months in series 1 and 3. In series 2 and 4, the titer dropped to 3.47 to 4.07 logs after seven months. At 37° C., series 1 to 4 showed a titer drop in the range of 1.37 to 2.77 logs after four weeks and in the range of 1.77 to 4.07 logs after 6 weeks.

Figure 6A:
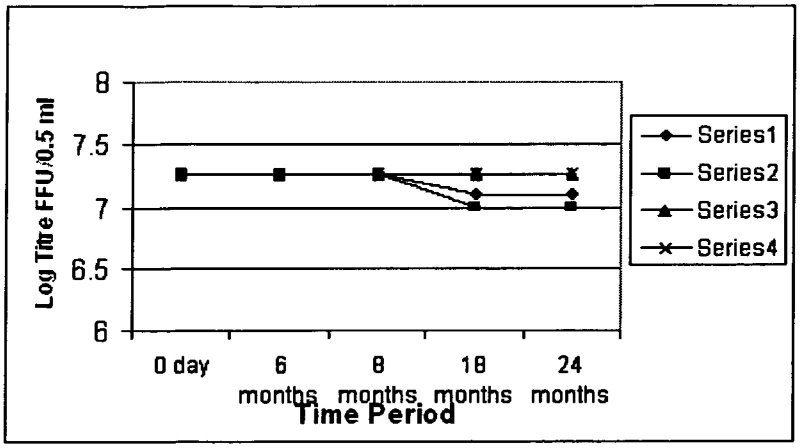
Figure 6B:
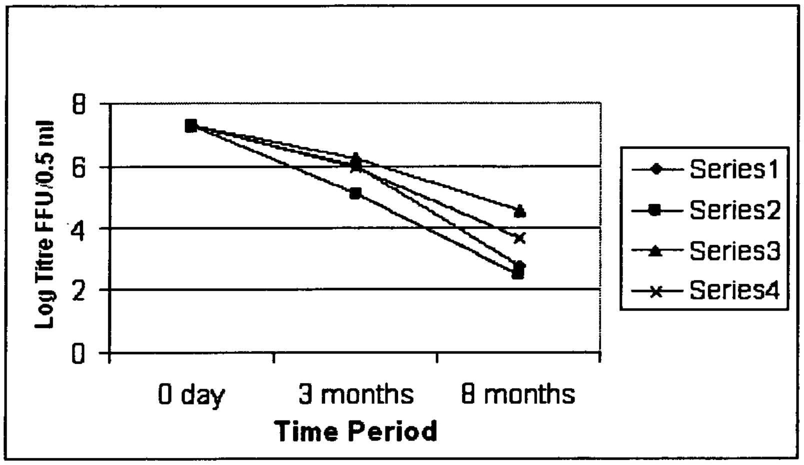
Figure 6C:
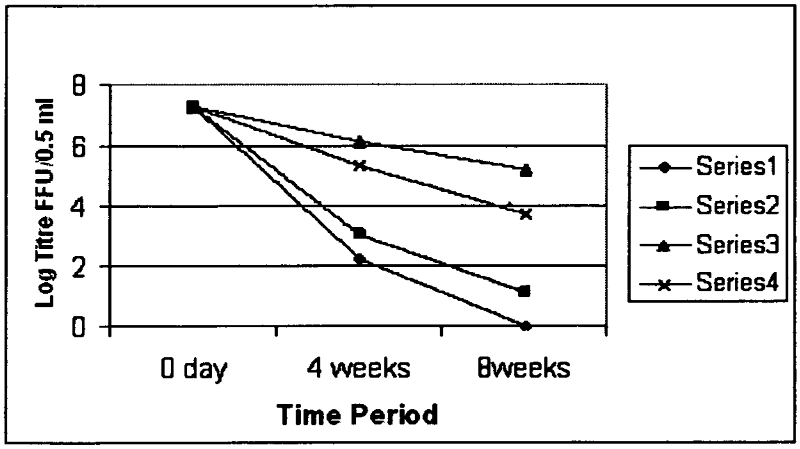

Shown in FIG. 6 is the stability data for the rotavirus 116 E liquid formulations at 2-8° C. (6A), 25° C. (6B) and 37° C. (6C). In each case, series 1 refers to a formulation with the combination of 0.5% lactalbumin hydrolysate, 10% of Soy protein and 1.0% of trehalose, series 2 refers to a formulation with the combination of 0.5% lactalbumin hydrolysate, 10% of soy protein and 1.0% of lactose, series 3 refers to a formulation with the combination of 5% lactalbumin hydrolysate, 2.5% of soy protein and 80% of sucrose, and series 4 refers to a formulation with the combination of 5% lactalbumin hydrolysate, 2.5% of soy protein and 50% of maltose. At 2-8° C., there was no titer drop in 3 and 4 series up to twenty four months and series 1 and 2 showed a negligible titer drop of 0.17 and 0.27 logs. At 25° C. series 1-4 showed a titer drop in the range of 1.07 to 2.17 logs after 3 months and a titer drop in the range of 2.7 to 4.47 logs after eight months. At 37° C. series 1 to 4 showed a titer drop in the range of 1.16 to 5.07 logs after four weeks and a titer drop in the range of 2.1 to 6.17 logs in series 2, 3 and 4 and nil in series 1 after eight weeks.

Figure 7A:
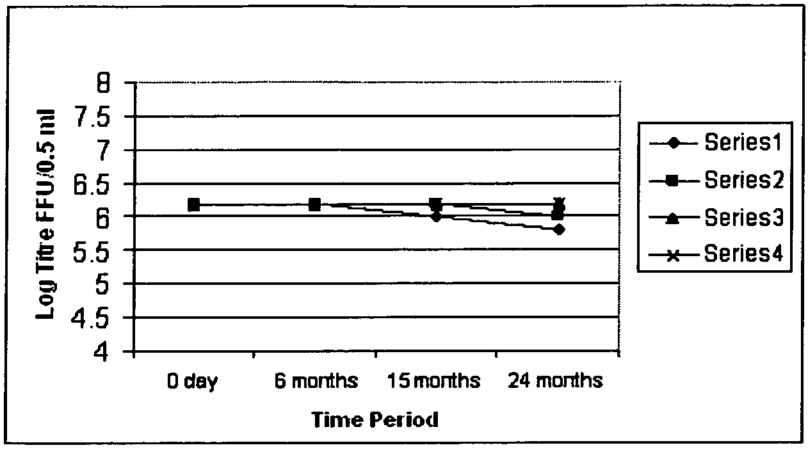
Figure 7B:
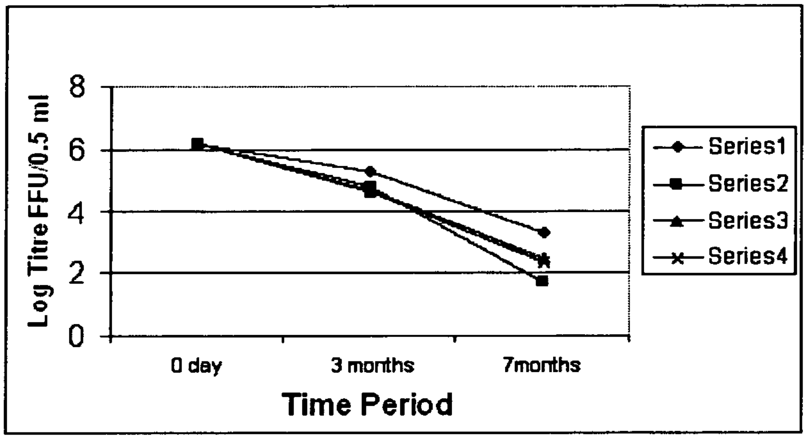
Figure 7C:
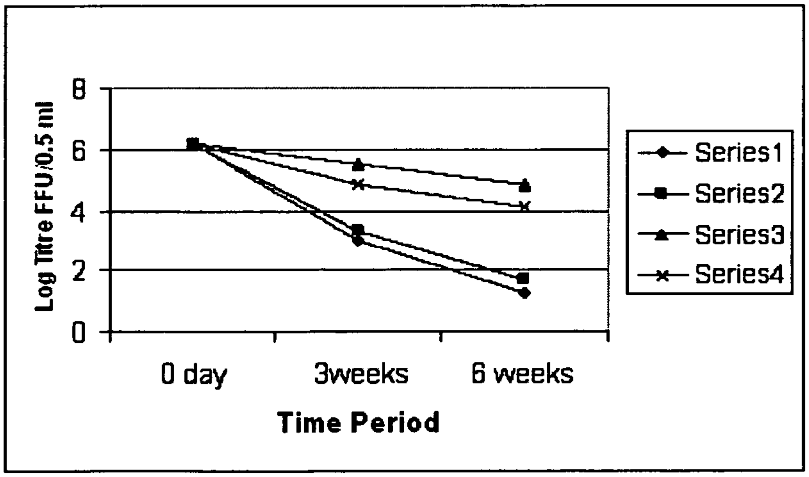

Shown in FIG. 7 is the high stability data for rotavirus 116 E liquid formulations at 2-8° C. (7A), 25° C. (7B) and 37° C. (7C). In each case, series 1 refers to a formulation with the combination of 10% lactalbumin hydrolysate, 10% of sucrose and 1.0% of trehalose, series 2 refers to a formulation with the combination of 10% lactalbumin hydrolysate, 5% of maltose and 1.0% of trehalose, series 3 refers to a formulation with the combination of 2.5% lactalbumin hydrolysate, 80% of sucrose and 1% of trehalose, and series 4 refers to a formulation with the combination of 2.5% lactalbumin hydrolysate, 50% of maltose and 1% of trehalose. At 2-8° C., there was no titer drop in 3 and 4 series up to twenty four months and series 1 and 2 showed 0.19 to 0.4 log drop after 15 months. At 25° C. series 1 to 4 showed a titer drop in the range of 0.89 to 1.59 logs after three months and a titer drop in the range of 2.89 to 4.49 logs after seven months. At 37° C., series 1 to 4 showed a titer drop in the range of 0.69 to 3.19 logs after four weeks and a titer drop in the range of 1.39 to 4.89 logs after six weeks.

Figure 8A:
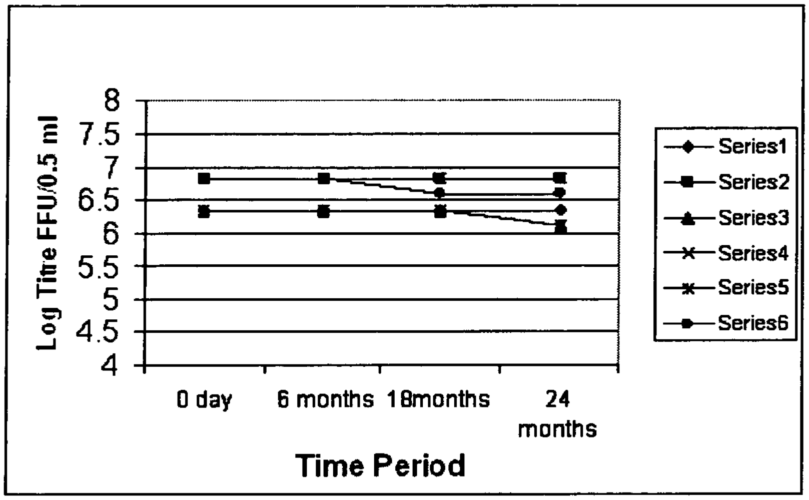
Figure 8B:
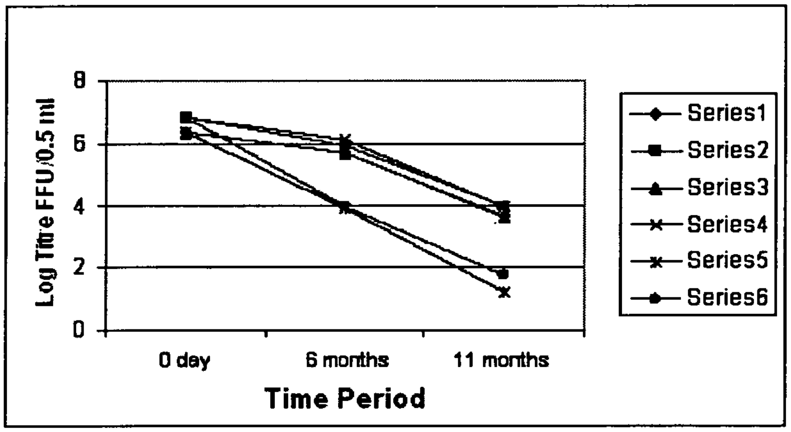
Figure 8C:
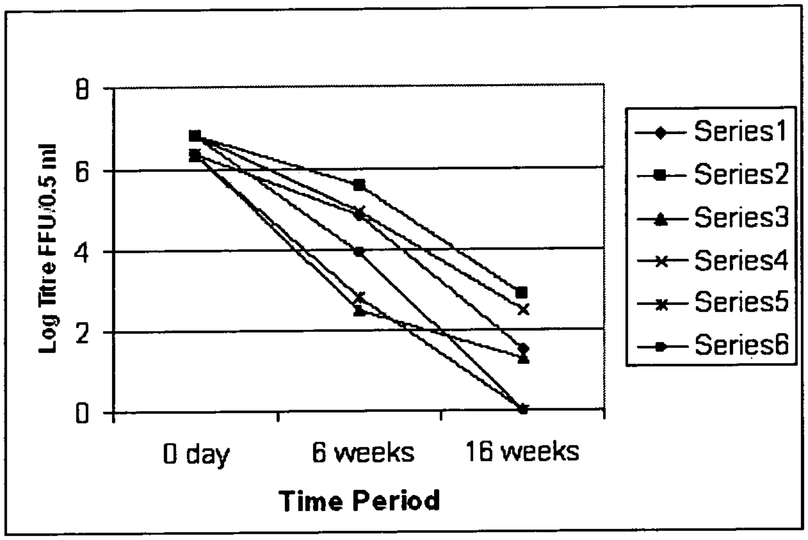

Shown in FIG. 8 is the high stability data for rotavirus 116 E liquid formulations at 2-8° C. (8A), 25° C. (8B) and 37° C. (8C). In each case, series 1 refers to a formulation with the combination of typical rotavirus, 5% of lactalbumin hydrolysate, 80% of sucrose and 0.5% of trehalose, series 2 refers to a formulation with the combination of pre-conditioned rotavirus, 5% lactalbumin hydrolysate, 80% of sucrose and 0.5% of trehalose, series 3 refers to a formulation with the combination of antigen from Bioprocess 1, 0.1% of HSA and 80% of sucrose, and 0.5% of trehalose and series 4 refers to a formulation with the combination of antigen from Bioprocess 2, 0.1% of HSA, 80% of sucrose and 0.5% of trehalose, series 4 refers to a formulation with the combination of antigen from Bioprocess 2, 0.1% of HAS, 80% of sucrose and 0.5% of trehalose, series 5 refers to a formulation with the combination of antigen from Bioprocess 1, 80% of sucrose and 0.5% of trehalose, series 6 refers to a formulation with the combination of antigen from Bioprocess 2, 80% of sucrose and 0.5% of trehalose. At 2°-8° C., there was no titer drop in series 1, 2 and 4 after 24 months and series 3, 5 and 6 showed no loss up to 18 months, and approximately 0.2 log drop was seen after 24 months. At 25° C., series 1, 2, 3 and 4 showed a titer drop in the range of 0.64 to 1.44 logs after six months and a titer drop in the range of 2.64 to 3.05 logs after eleven months. Series 5 and 6 showed a titer drop in the range of 2.44 and 2.82 after six months and 5.09 and 5.02 logs drop after 11 months. At 37° C. series 1, 2, 3 and 4 show a titer drop in the range of 1.51 to 4.83 logs after six weeks and a titer drop in the range of 4.0 to 5.04 logs after sixteen weeks. Series 5 & 6 showed a titer drop in the range of 2.92 to 3.54 logs after six weeks and became nil after sixteen weeks.

Figure 9:
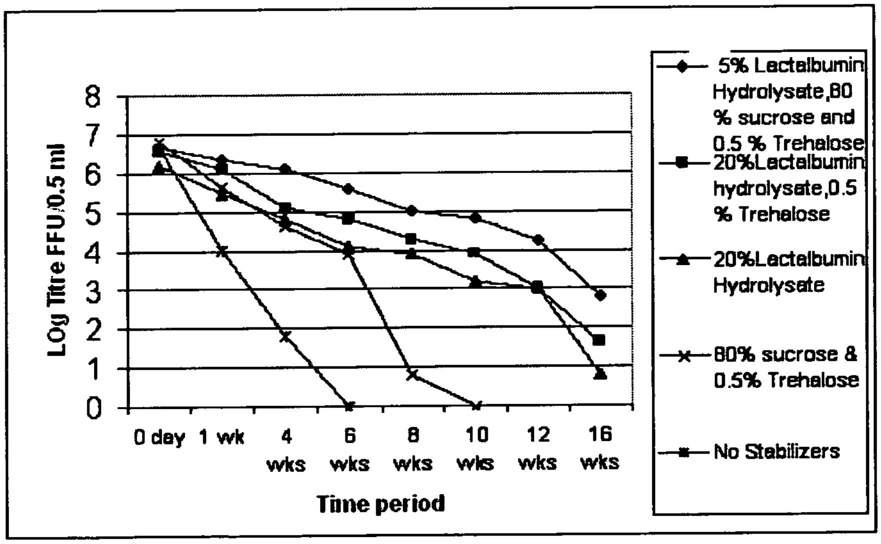

Shown in FIG. 9 is the stability data for the rotavirus in five different formulations at 37 C. The formulation which had no stabilizer showed a deep fall in the titer value and became nil after six weeks. The Final Bulk which was pre-conditioned virus with 80% sucrose and 0.5% trehalose dropped 2.2 logs after 4 weeks, 2.92 logs after six weeks, 6.02 logs after 8 weeks and became nil after ten weeks. The Final Bulk with 20% of lactalbumin hydrolysate showed 1.39 log drop after four weeks, 2.09 logs drop after six weeks, 2.29 logs after eight weeks and 5.39 logs drop after 16 weeks. The Final Bulk with 20% lactalbumin hydrolysate and 0.5% trehalose showed a titre drop of 4.97 after 16 weeks. The Final Bulk with a combination of 5% lactalbumin hydrolysate, 80% sucrose and 0.5% trehalose showed gradual drop from first week to 16th week; 1.1 logs drop after 6 weeks, 2.42 logs drop after 12 weeks and 3.85 logs drop after 16 weeks. When the bulk was formulated with 80% sucrose, 0.5% trehalose, the stability of the vaccine at 37 C was seen up to one week and slow degradation up to four weeks and a sharp fall after six weeks. The bulk formulated with 20% lactalbumin hydrolysate showed better stability and is able to hold up to four weeks with less than 1.5 log drop in titer and gradual fall in titer is seen up to 16 weeks. Not so dramatic drop in titer was seen with 20% Lactalbumin hydrolysate and 0.5% trehalose after 16 weeks at 37 when compared to the vaccine with 20% lactalbumin alone. When the bulk was formulated with 5% lactalbumin hydrolysate, 80% sucrose and 0.5% trehalose, less than 1.5 log drop after six weeks and 3.85 logs drop after 16 weeks was seen.

Figure 10A:
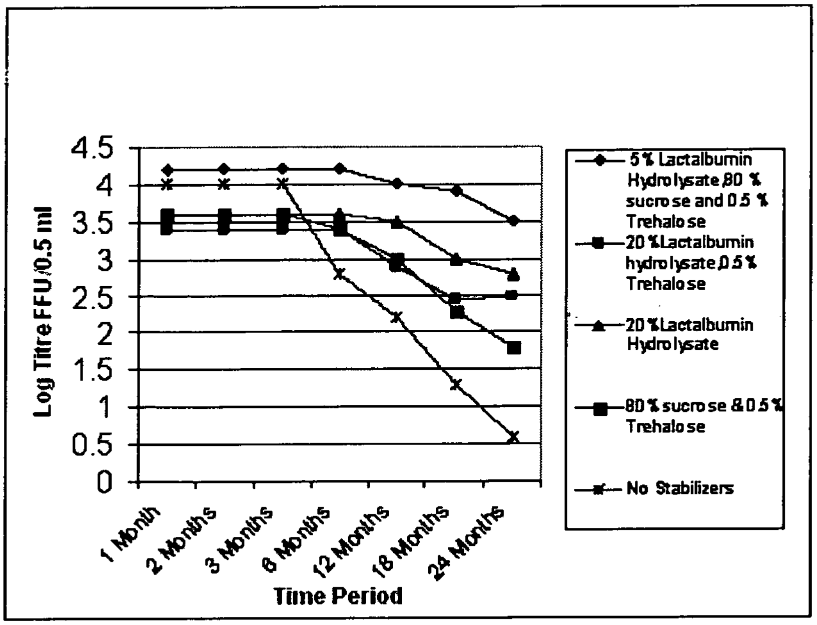
Figure 10B:
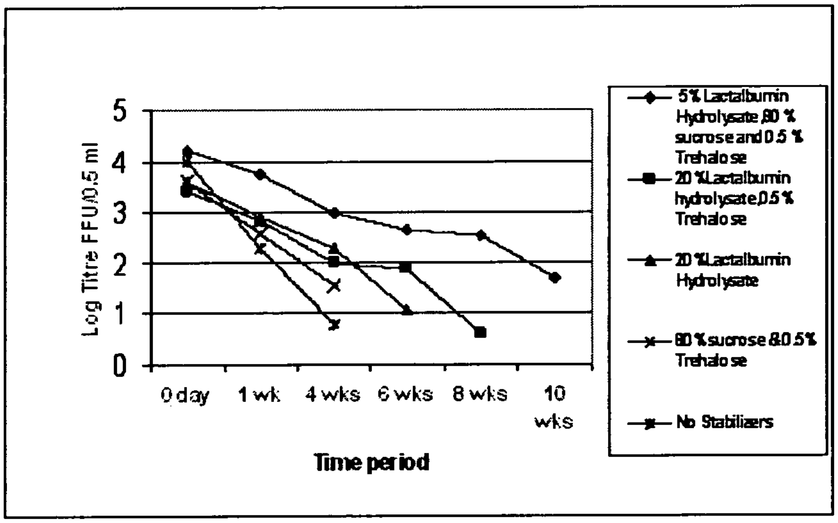
Figure 11A:
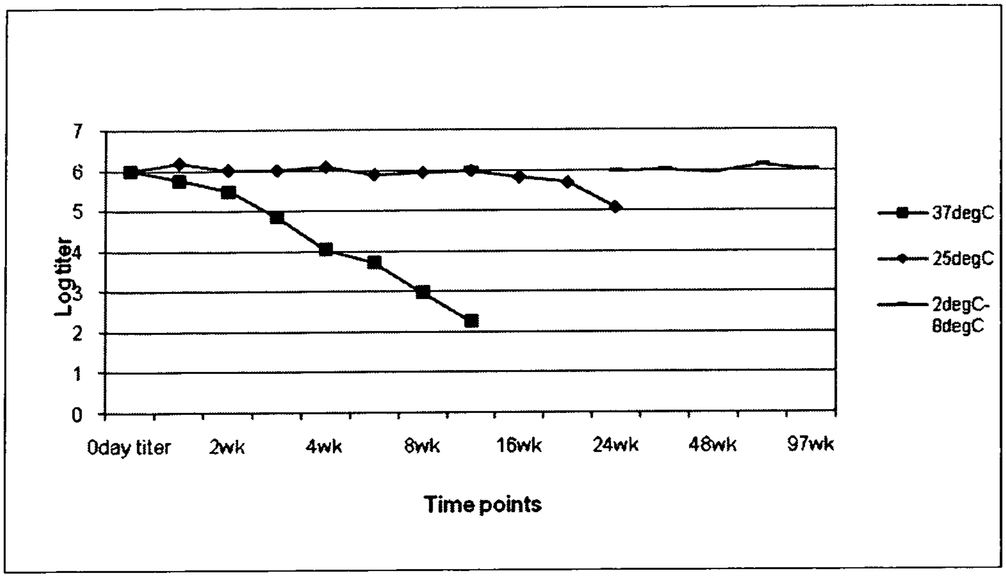
FIG. 11A (Liq) shows stability data for pre-conditioned rota virus formulations containing 20% hydrolysed peptone at 2-8° C., 25° C., and 37° C.
Figure 11B:
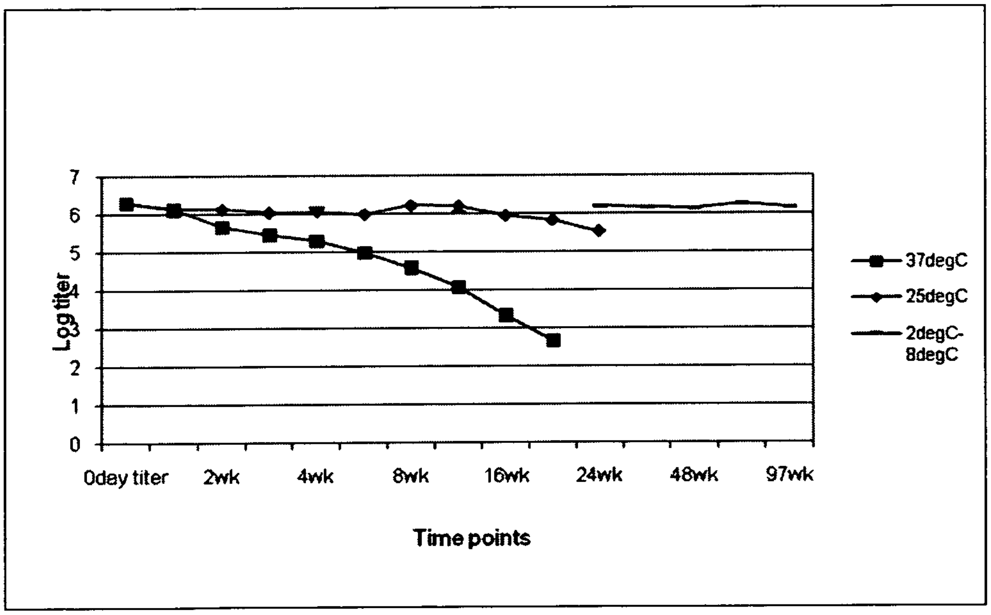
FIG. 11B (Liq) shows stability data for pre-conditioned rota virus formulations containing a combination of 20% hydrolysed peptone, 1% Trehalose, and 0.02% Fucose at 2-8° C., 25° C., and 37° C.
Figure 11C:
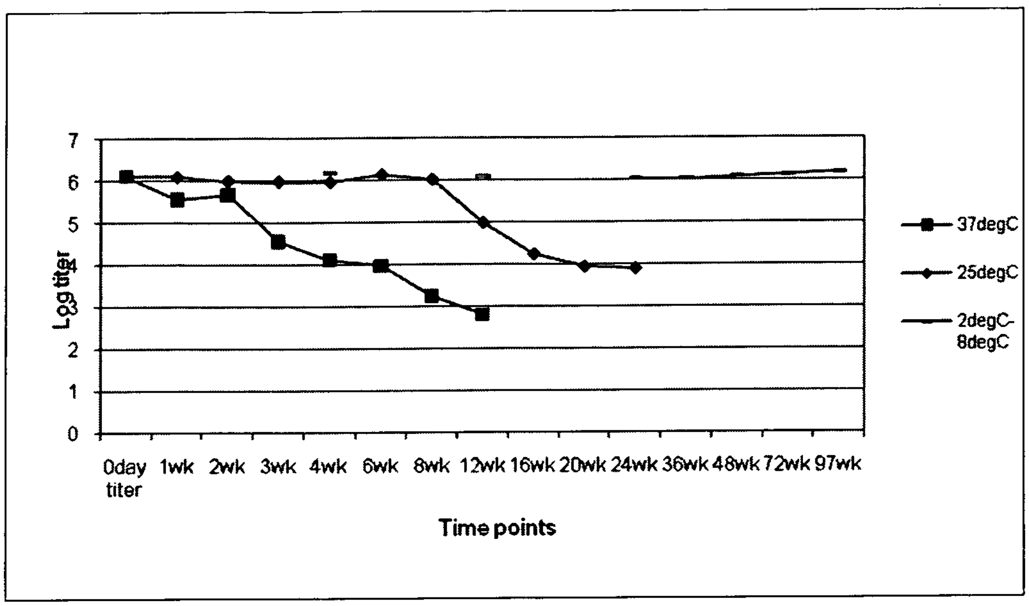
FIG. 11C (Liq) shows stability data for the pre-conditioned rota virus formulations containing 20% Egg protein hydrolysate at 2-8° C., 25° C., and 37° C.
Figure 11D:
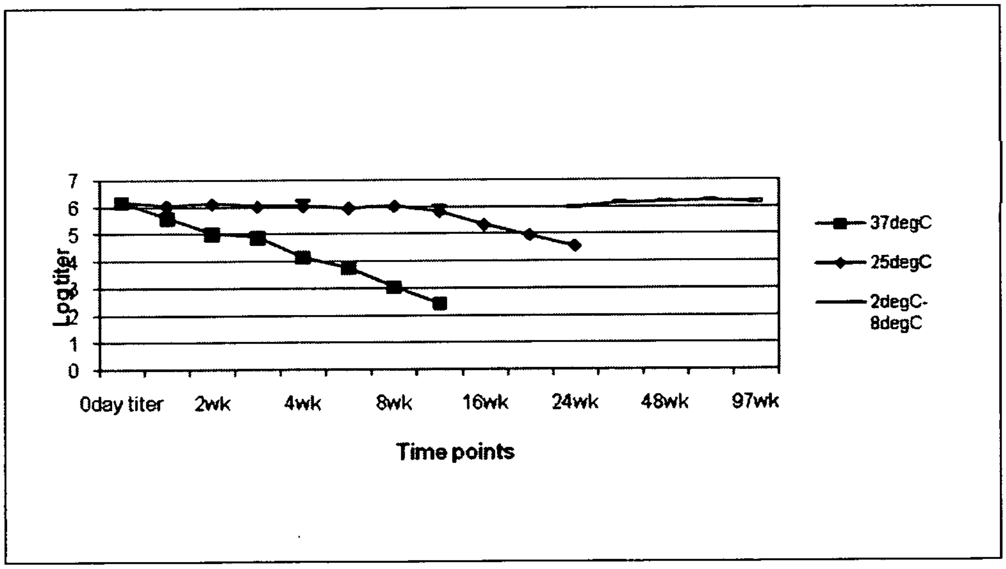
FIG. 11D (Liq) shows stability data for pre-conditioned rota virus formulations containing a combination of 20% Egg protein hydrolysate, 0.5% Trehalose, 1% D-Sorbitol, and 0.5% Mannose at 2-8° C., 25° C., and 37° C.
Figure 11E:
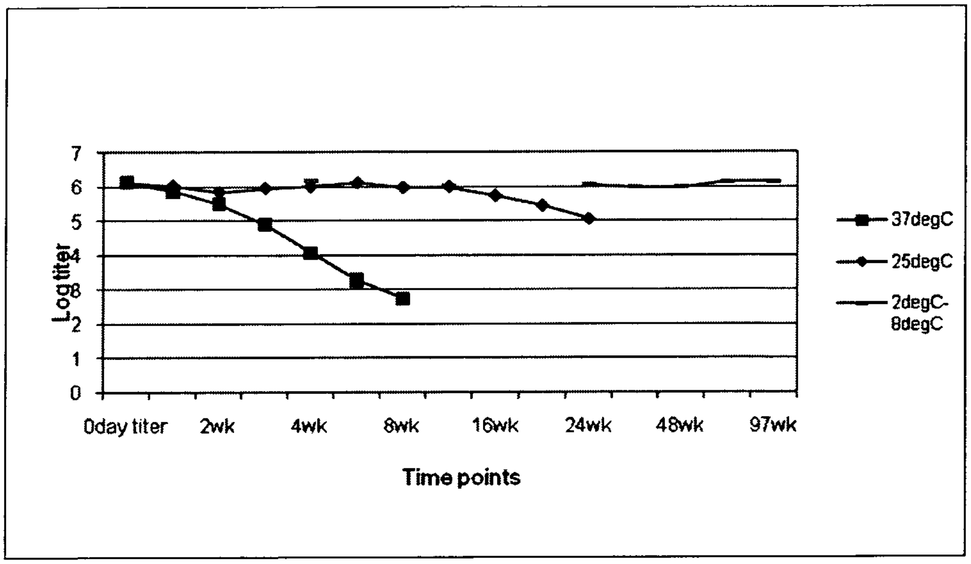
FIG. 11E (Liq) shows stability data for pre-conditioned rota virus formulations containing 20% Lactalbumin hydrolysate at 2-8° C., 25° C., and 37° C.
Figure 11F:
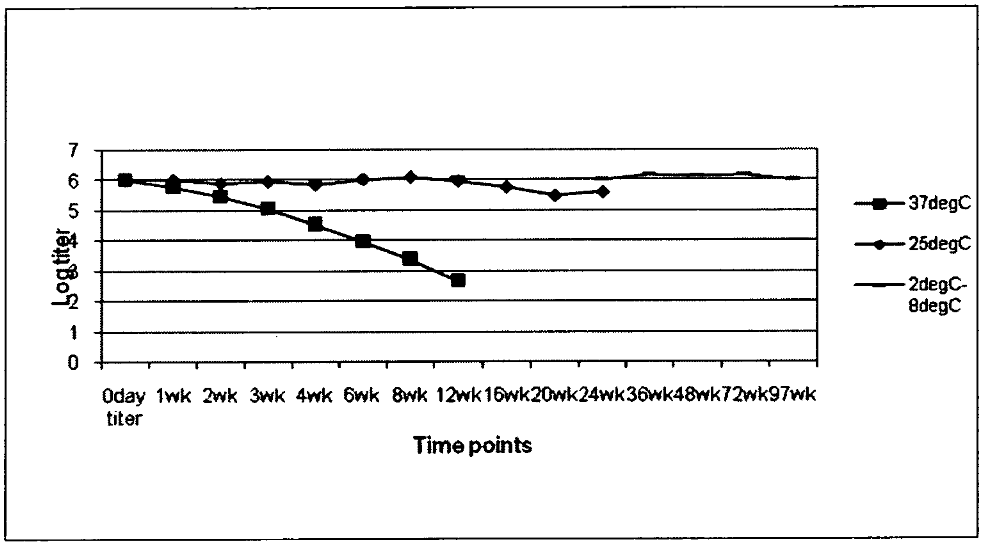
FIG. 11F (Liq) shows stability data for pre-conditioned rota virus formulations containing a combination of 20% Lactalbumin hydrolysate, 0.5% Trehalose, at 2-8° C., 25° C., and 37° C.
Figure 11G:
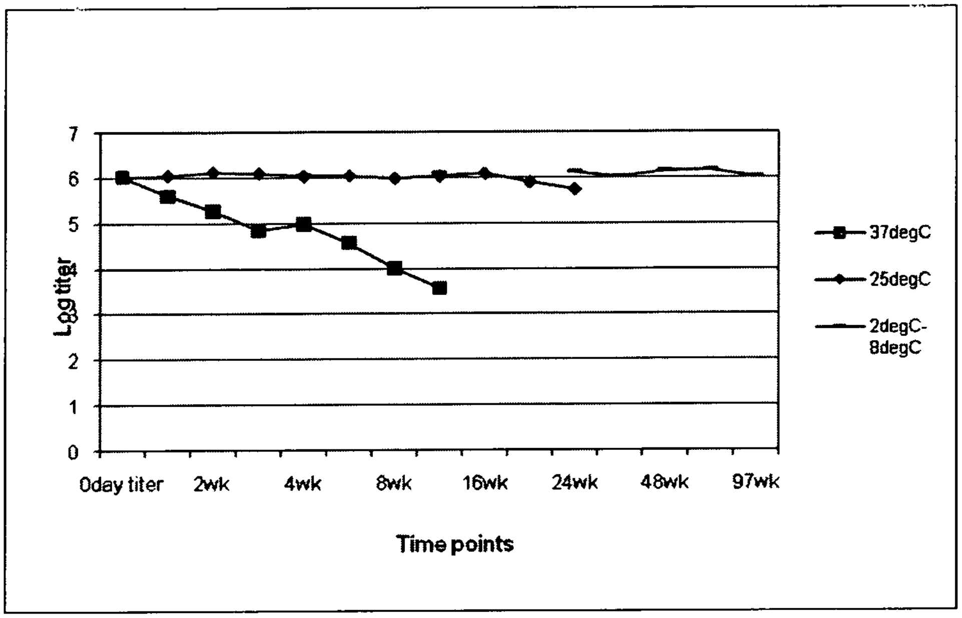
FIG. 11G (Liq) shows stability data for pre-conditioned rota virus formulations containing 20% Yeast hydrolysate at 2-8° C., 25° C., and 37° C.
Figure 11H:
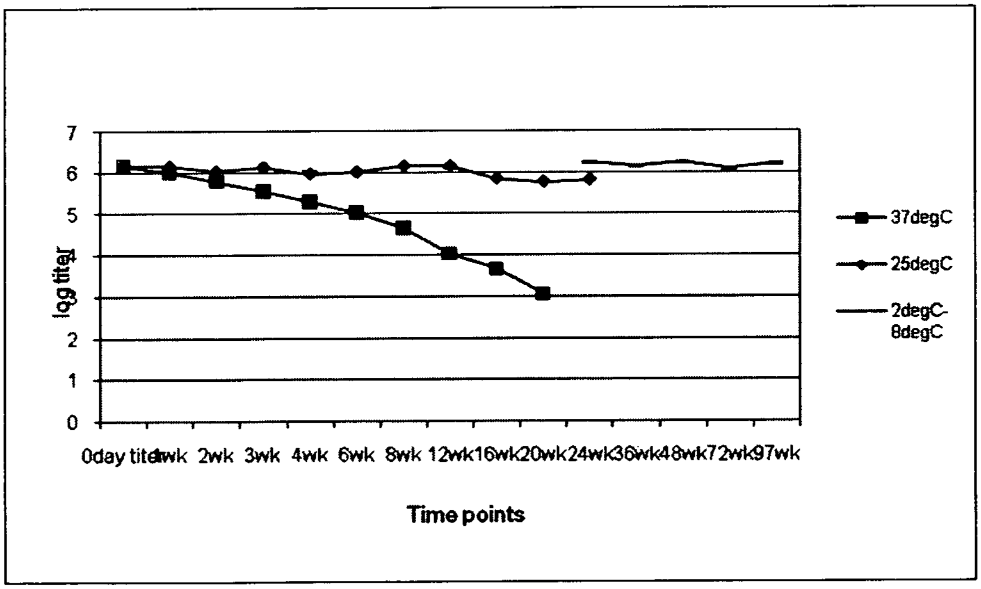
FIG. 11H (Liq) shows stability data for pre-conditioned rota virus formulations containing a combination of 20% Yeast hydrolysate, 5% Maltose, and 0.5% Lactose at 2-8° C., 25° C., and 37° C.
Figure 12A:
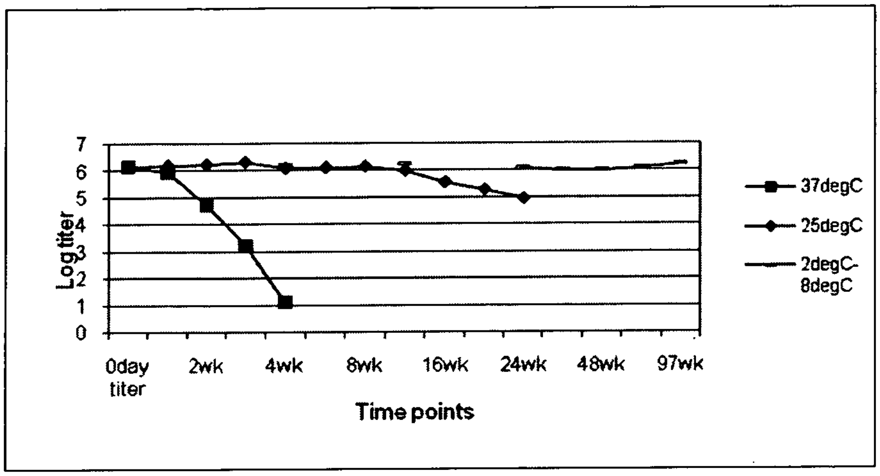
FIG. 12A (Liq) shows stability data for typical rota virus formulations containing 20% hydrolysed peptone at 2-8° C., 25° C., and 37° C.
Figure 12B:
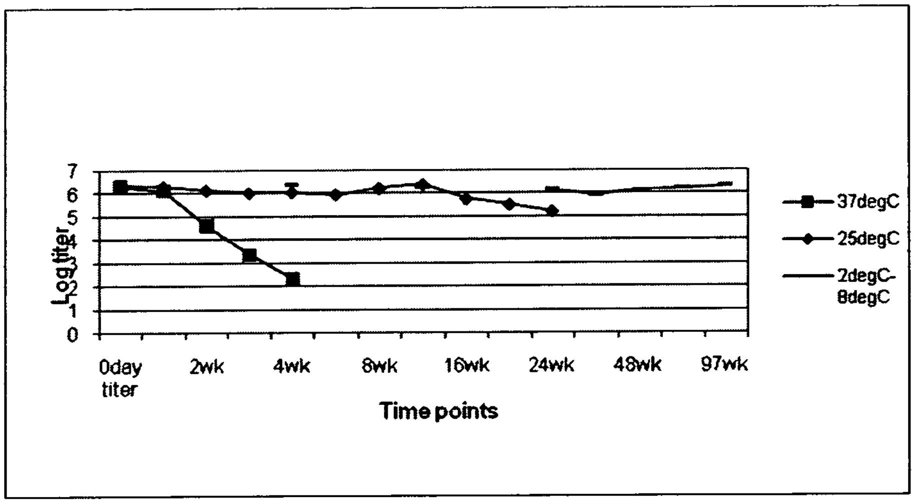
FIG. 12B (Liq) shows stability data for typical rota virus formulations containing a combination of 20% hydrolysed peptone, 1% Trehalose, and 0.02% Fucose at 2-8° C., 25° C., and 37° C.
Figure 12C:
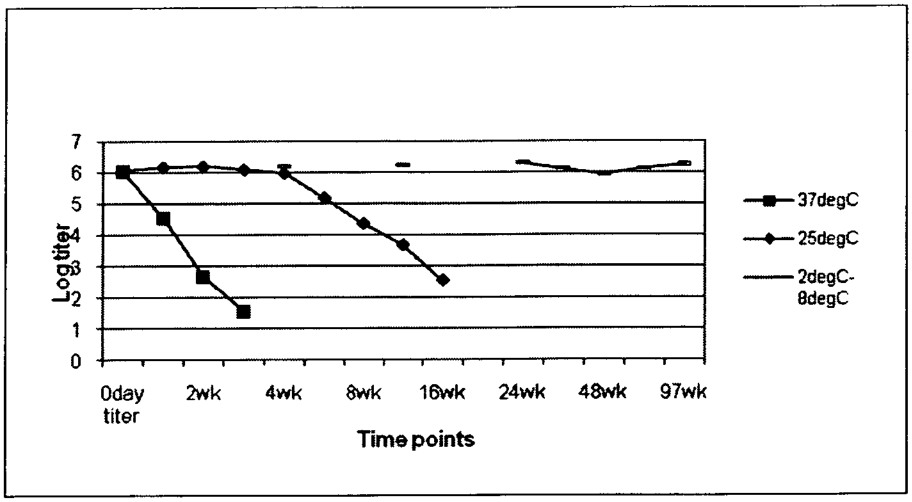
FIG. 12C (Liq) shows stability data for the typical rota virus formulations containing 20% Egg protein hydrolysate at 2-8° C., 25° C., and 37° C.
Figure 12D:
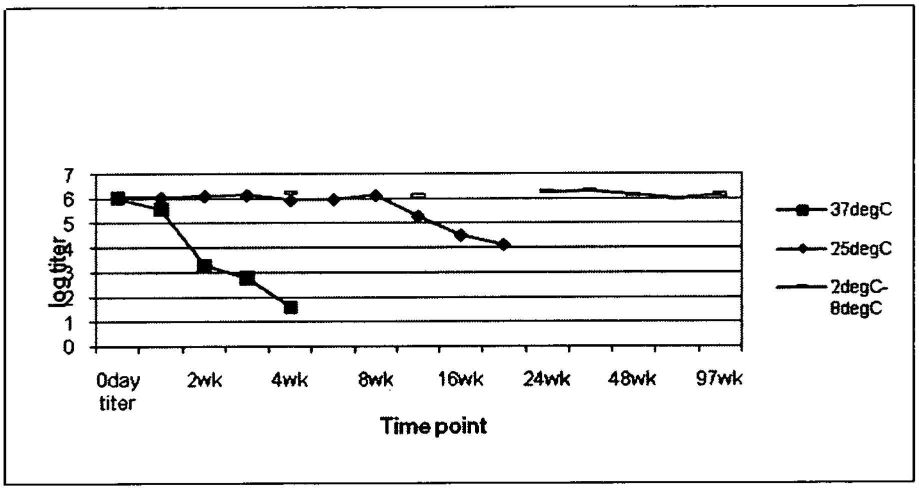
FIG. 12D (Liq) shows stability data for typical rota virus formulations containing a combination of 20% Egg protein hydrolysate, 0.5% Trehalose, 1% D-Sorbitol, and 0.5% Mannose at 2-8° C., 25° C., and 37° C.
Figure 12E:
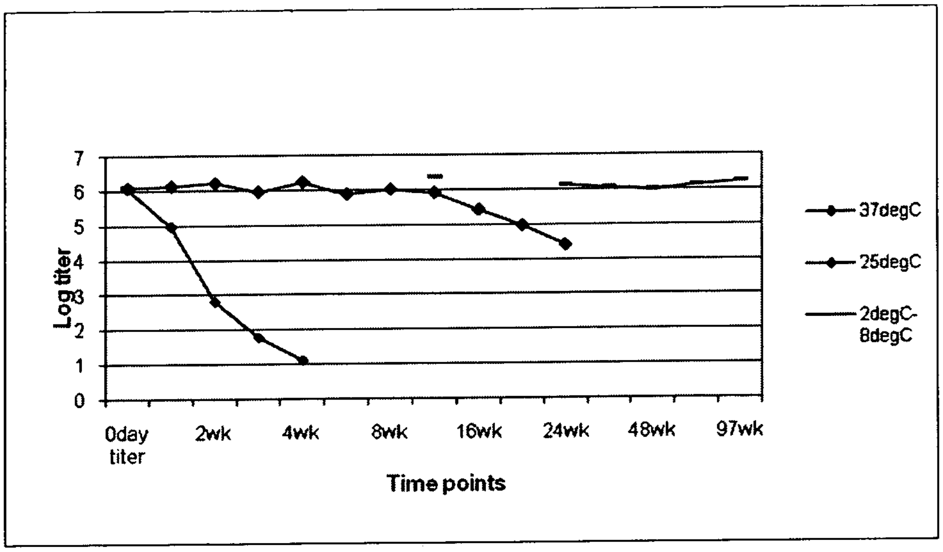
FIG. 12E (Liq) shows stability data for typical rota virus formulations containing 20% Lactalbumin hydrolysate at 2-8° C., 25° C., and 37° C.
Figure 12F:
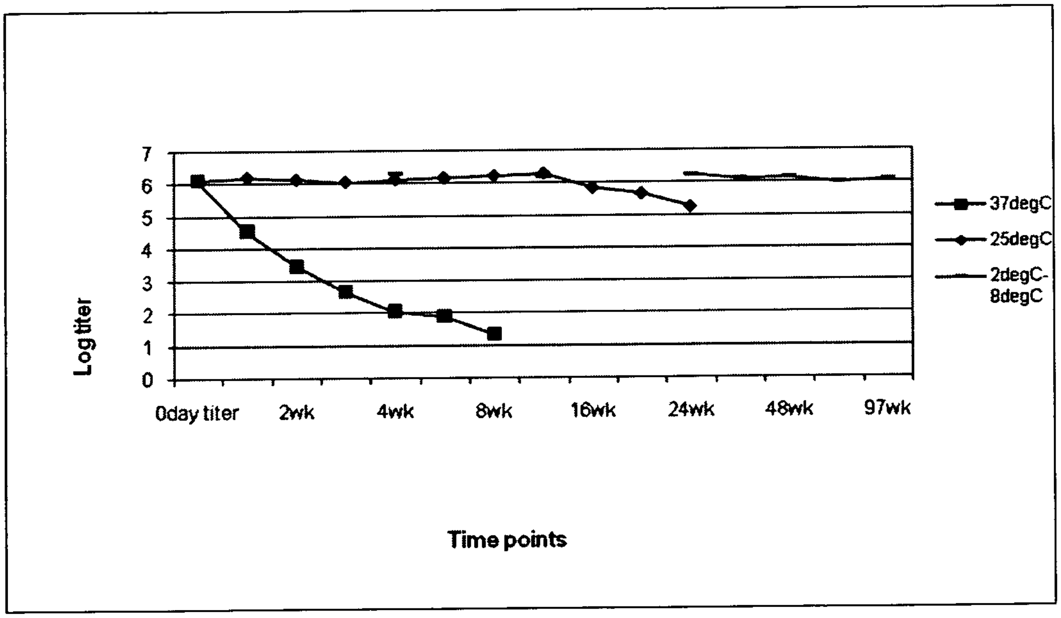
FIG. 12F (Liq) shows stability data for typical rota virus formulations containing a combination of 20% Lactalbumin hydrolysate, 0.5% Trehalose, at 2-8° C., 25° C., and 37° C.
Figure 12G:
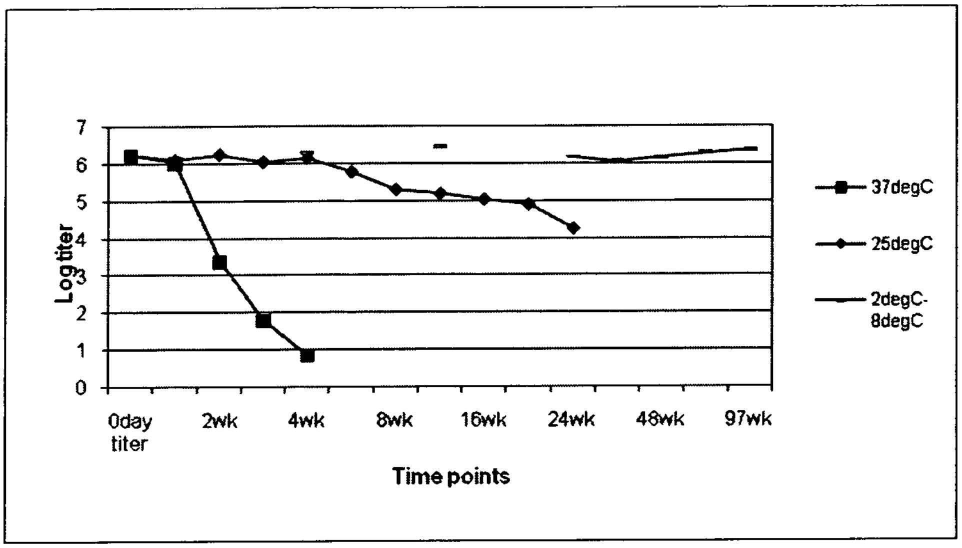
FIG. 12G (Liq) shows stability data for typical rota virus or ulations containing 20% Yeast hydrolysate at 2-8° C., 25° C., and 37° C.
Figure 12H:
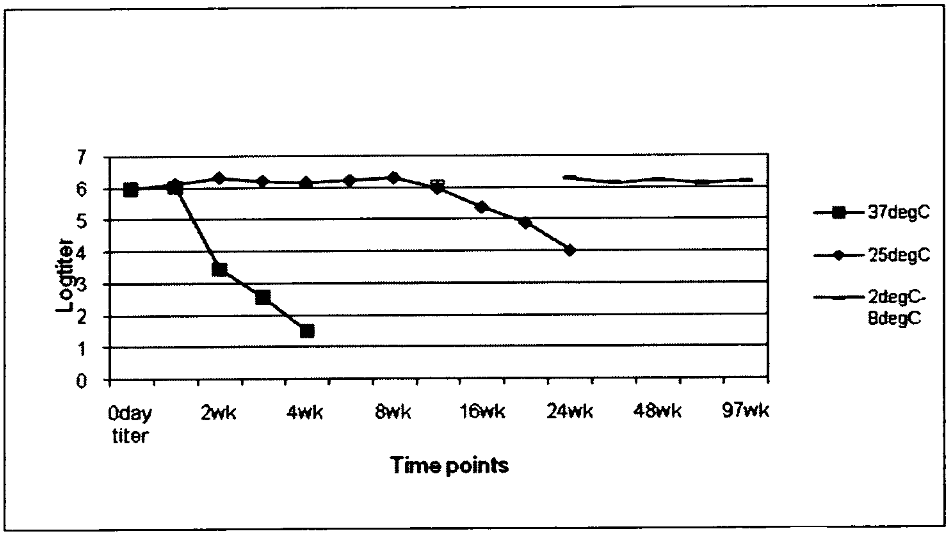
Figure 13A:
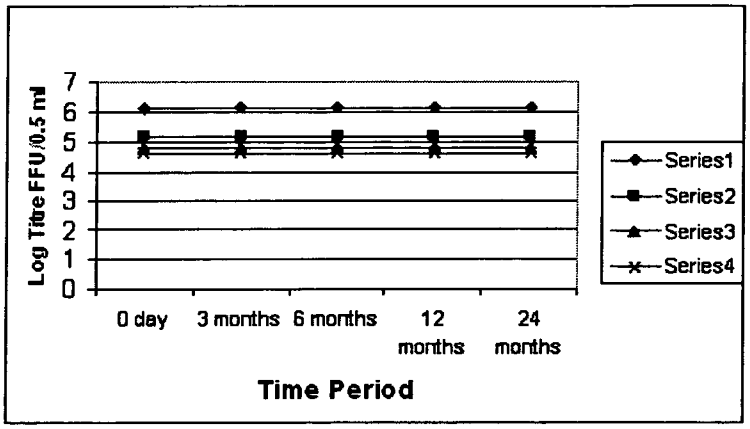
FIGS. 13A-17C show data for lyophilized formulations (Lyo=lyophilized). The numbers expressed in percentages represent values by weight of the formulation (composition). For example, 80% sucrose should be understood to mean 80% sucrose by weight of the formulation (w/v). The standard error for all time points ranged from ±0.40 to ±0.45.
Figure 13B:
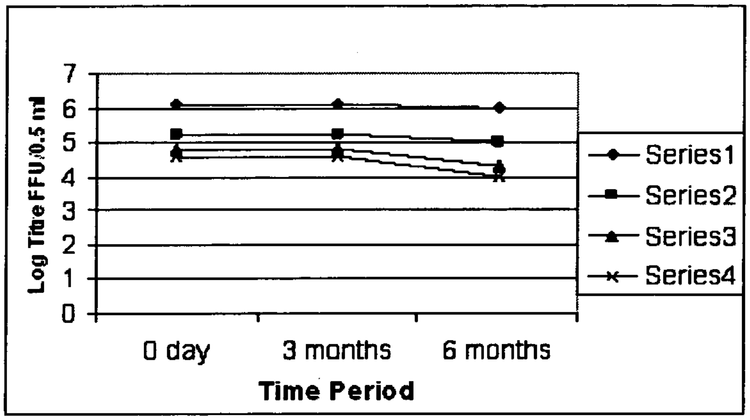
Figure 13C:
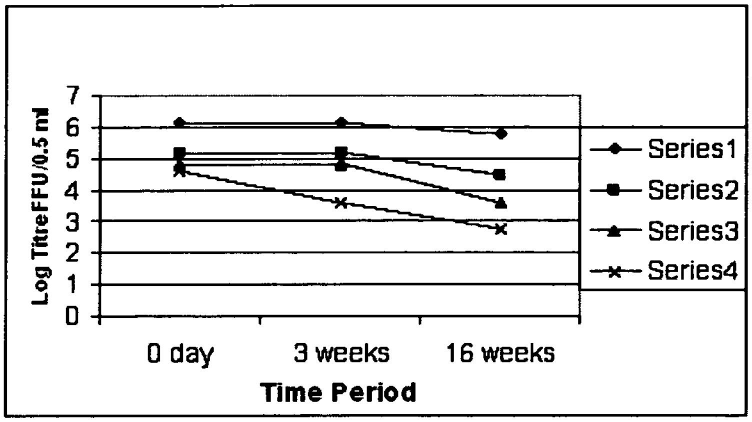
Figure 14A:
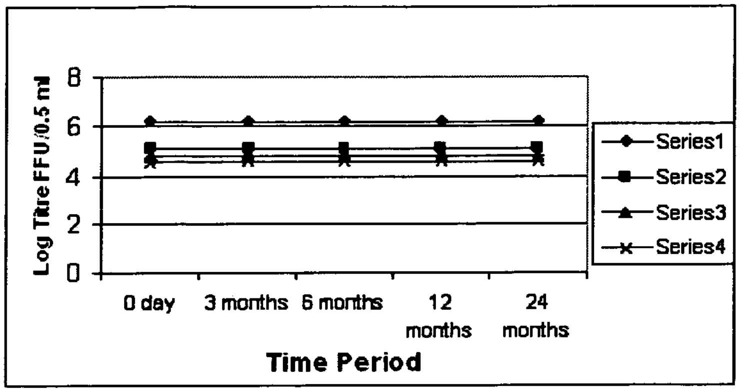
Figure 14B:
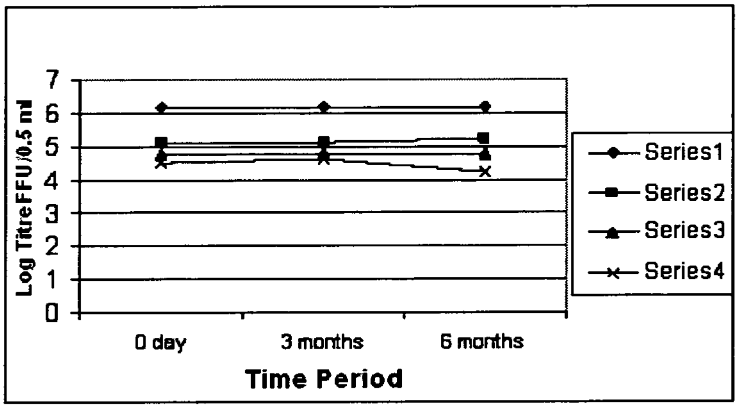
Figure 14C:
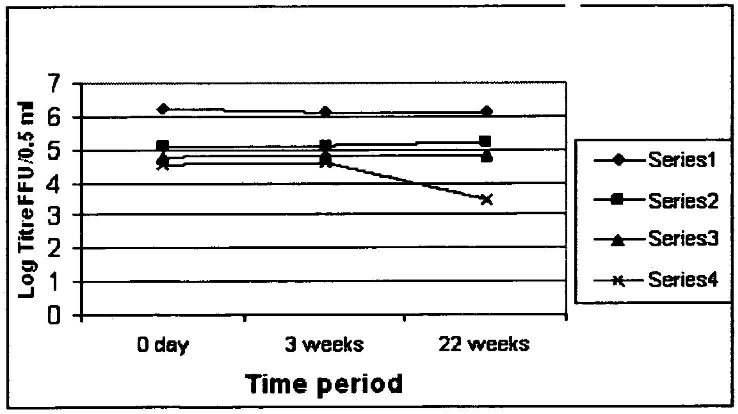
Figure 15A:
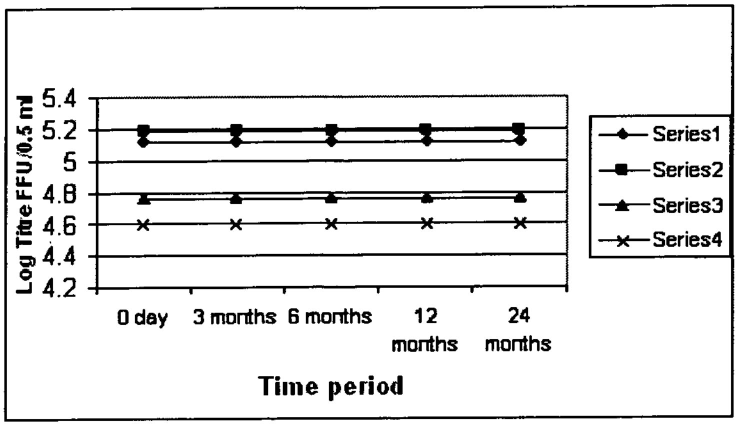
Figure 15B:
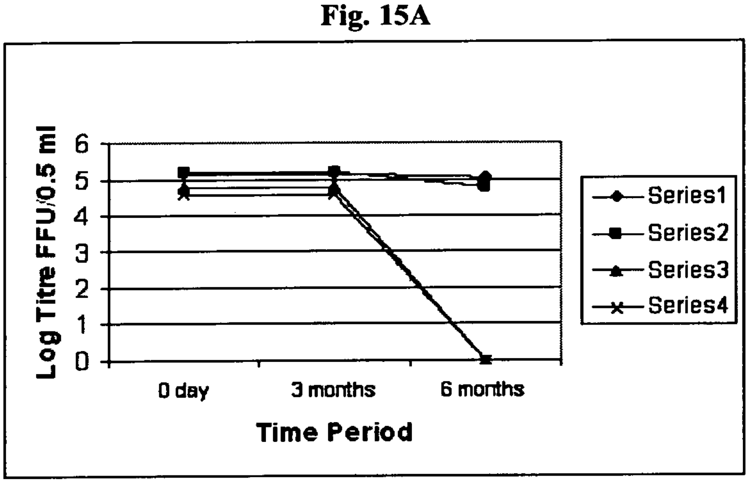
Figure 15C:
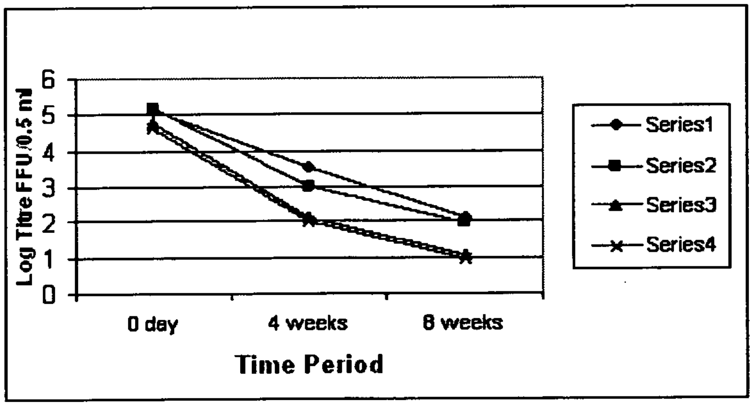
Figure 16A:
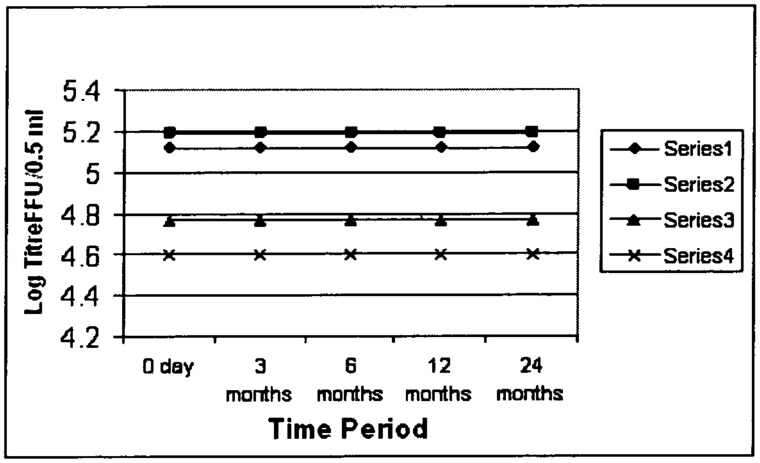
Figure 16B:
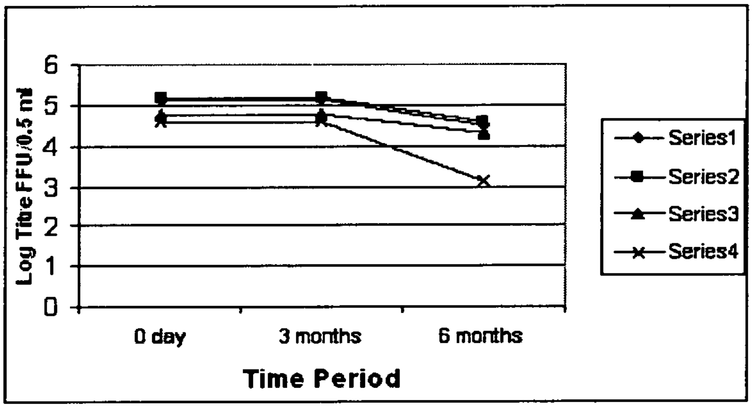
Figure 16C:
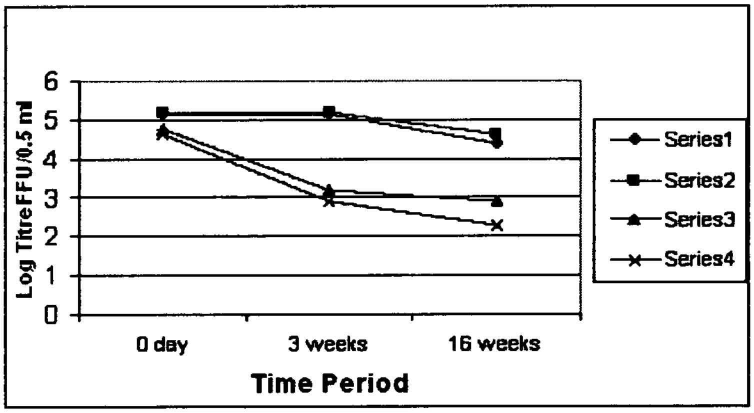
Figure 17A:
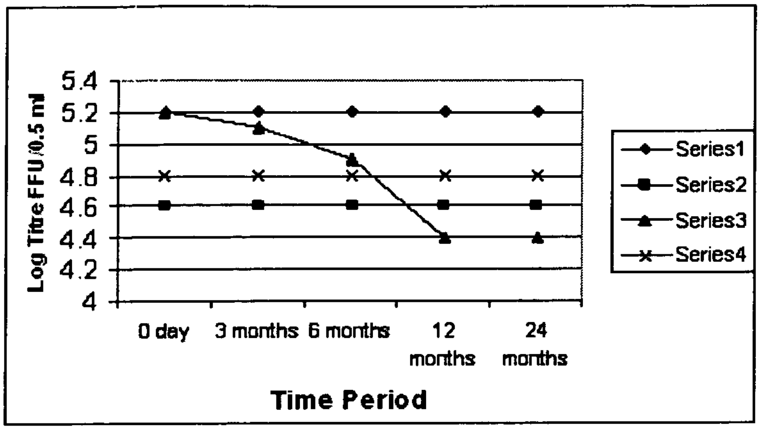
Figure 17B:
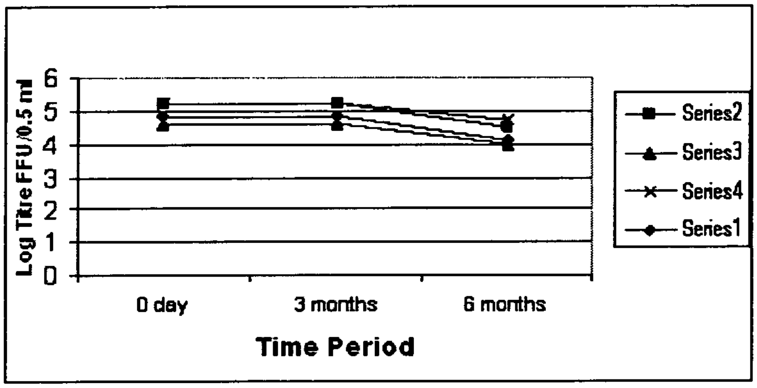
Figure 17C:
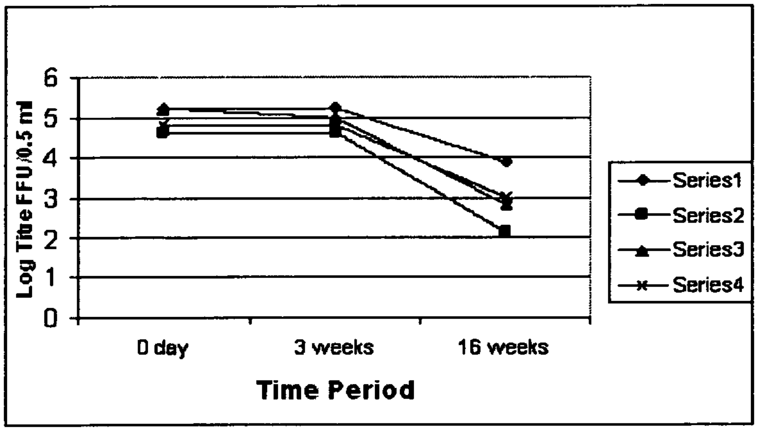

Shown in FIG. 10 is the stability for the low titer (less than $10^4$) rotavirus vaccine in five different formulations at 2-8° C. (10A) and 37° C. (10B). At 2-8° C., the formulation which had no stabilizer showed a fall in the titer value and became 0.6 after 24 months. The formulation with 80% sucrose and 0.5% trehalose showed 1.8 log drop after 24 months, the formulation with 20% lactalbimin hydrolysate and the formulation with 20% lactalbumin hydrolysate and 0.5% trehalose showed 0.8 log and 0.89 logs drop, and the formulation with 5% lactalbumin hydrolysate, 80% sucrose and 0.5% trehalose showed 0.7 log drop in titer after 24 months. At 37° C., the formulation which had no stabilizer showed a deep fall in the titer value and became 0.8 after four weeks. The Final Bulk which was formulated with 80% sucrose and 0.5% trehalose dropped 2.06 logs after 4 weeks, whereas the bulk with 20% of lactalbumin hydrolysate showed 2.48 logs drop after six weeks, the bulk formulated with 20% lactalbumin hydrolysate and 0.5% trehalose showed a titer drop of 2.79 after 8 weeks. The Final Bulk that was formulated with a combination of 5% lactalbumin hydrolysate, 80% sucrose and 0.5% trehalose showed gradual drop from first week to the $10^{th}$ week; a 1.2 log drop was seen after 4 weeks, 1.7 logs drop after 8 weeks and 2.5 logs drop after 10 weeks. FIG. 10 demonstrates the fact that lactalbumin hydrolysate at particular concentrations definitely improves the stability of low titer rotavirus vaccines at 37° C.

Shown in FIGS. 11A to 11H is the stability data for liquid formulations of pre-conditioned virus with different stabilizers. The same is reproduced below in Table 3

Shown in FIGS. 12A to 12H is the stability data for liquid formulations of typical virus with different stabilizers. The same is reproduced below in Table 4.

TABLE 3

| | 0 day titer | 1 wk | 2 wk | 3 wk | 4 wk | 6 wk | 8 wk | 12 wk | 16 wk | 20 wk | 24 wk | 36 wk | 48 wk | 72 wk | 97 wk |
|---|---|---|---|---|---|---|---|---|---|---|---|---|---|---|---|
| Rotavirus 116E liquid formulations<br>Formulation details<br>Peptone hydrolysed - 20% | | | | | | | | | | | | | | | |
| 37 deg C. | 5.99 | 5.75 | 5.48 | 4.85 | 4.05 | 3.72 | 2.98 | 2.26 | | | | | | | |
| 25 deg C. | 5.99 | 6.18 | 6.01 | 6 | 6.08 | 5.89 | 5.94 | 5.98 | 5.82 | 5.69 | 5.08 | | | | |
| 2 deg C.-8 deg C. | 5.99 | | | | 6.02 | | | 6.05 | | | 5.97 | 6.01 | 5.95 | 6.13 | 6.02 |
| Formulation details<br>Peptone hydrolysed - 20%<br>Trehalose - 1%<br>Fucose - 0.02% | | | | | | | | | | | | | | | |
| 37 deg C. | 6.28 | 6.11 | 5.65 | 5.45 | 5.28 | 4.97 | 4.57 | 4.05 | 3.32 | 2.65 | | | | | |
| 25 deg C. | 6.28 | 6.12 | 6.13 | 6.03 | 6.05 | 5.98 | 6.21 | 6.2 | 5.94 | 5.82 | 5.52 | | | | |
| 2 deg C.-8 deg C. | 6.28 | | | | 6.15 | | | 6.02 | | | 6.17 | 6.15 | 6.12 | 6.25 | 6.16 |
| Formulation details<br>Egg protein hydrolysate - 20% | | | | | | | | | | | | | | | |
| 37 deg C. | 6.11 | 5.56 | 5.68 | 4.56 | 4.11 | 3.98 | 3.25 | 2.81 | 6.11 | 5.56 | | | | | |
| 25 deg C. | 6.11 | 6.1 | 6 | 5.98 | 5.97 | 6.14 | 6.02 | 4.99 | 4.25 | 3.95 | 3.9 | | | | |
| 2 deg C.-8 deg C. | 6.11 | | | | 6.18 | | | 6.1 | | | 6.03 | 6.04 | 6.08 | 6.12 | 6.18 |
| Formulation details<br>Egg protein hydrolysate - 20%<br>Trehalose0.5%<br>D-Sorbitol - 1%<br>Mannose - 0.5% | | | | | | | | | | | | | | | |
| 37 deg C. | 6.17 | 5.58 | 5.02 | 4.89 | 4.15 | 3.75 | 3.05 | 2.45 | | | | | | | |
| 25 deg C. | 6.17 | 6.05 | 6.12 | 6.03 | 6.05 | 5.97 | 6.04 | 5.84 | 5.34 | 4.97 | 4.56 | | | | |
| 2 deg C.-8 deg C. | 6.17 | | | | 6.23 | | | 6.04 | | | 6 | 6.15 | 6.19 | 6.23 | 6.17 |

TABLE 3-continued

| | 0 day titer | 1 wk | 2 wk | 3 wk | 4 wk | 6 wk | 8 wk | 12 wk | 16 wk | 20 wk | 24 wk | 36 wk | 48 wk | 72 wk | 97 wk |
|---|---|---|---|---|---|---|---|---|---|---|---|---|---|---|---|
| Formulation details<br>Lactalbumin Hydrolysate - 20% | | | | | | | | | | | | | | | |
| 37 deg C. | 6.08 | 4.96 | 2.81 | 1.78 | 1.12 | | | | | | | | | | |
| 25 deg C. | 6.08 | 6.12 | 6.21 | 5.96 | 6.22 | 5.89 | 6.01 | 5.92 | 5.43 | 4.98 | 4.42 | | | | |
| 2 deg C.-8 deg C. | 6.08 | | | | 6.18 | | | 6.36 | | | 6.11 | 6.06 | 5.99 | 6.12 | 6.23 |
| Formulation details<br>Lactalbumin Hydrolysate - 20%<br>Trehalose - 0.5% | | | | | | | | | | | | | | | |
| 37 deg C. | 6.12 | 4.56 | 3.46 | 2.66 | 2.06 | 1.89 | 1.35 | | | | | | | | |
| 25 deg C. | 6.12 | 6.21 | 6.15 | 6.06 | 6.13 | 6.18 | 6.25 | 6.31 | 5.85 | 5.67 | 5.26 | | | | |
| 2 deg C.-8 deg C. | 6.12 | | | | 6.32 | | | 6.21 | | | 6.26 | 6.11 | 6.15 | 6.01 | 6.07 |
| Formulation details<br>Yeast Hydrolysate - 20% | | | | | | | | | | | | | | | |
| 37 deg C. | 6.22 | 6.01 | 3.35 | 1.76 | 0.83 | | | | | | | | | | |
| 25 deg C. | 6.22 | 6.1 | 6.23 | 6.03 | 6.13 | 5.76 | 5.28 | 5.18 | 5.02 | 4.89 | 4.24 | | | | |
| 2 deg C.-8 deg C. | 6.22 | | | | 6.28 | | | 6.45 | | | 6.16 | 6.04 | 6.15 | 6.27 | 6.35 |
| Formulation details<br>Yeast Hydrolysate - 20%<br>Maltose - 5%<br>Lactose - 0.5% | | | | | | | | | | | | | | | |
| 37 deg C. | 5.98 | 6.03 | 3.45 | 2.58 | 1.52 | | | | | | | | | | |
| 25 deg C. | 5.98 | 6.13 | 6.32 | 6.22 | 6.18 | 6.23 | 6.31 | 5.98 | 5.38 | 4.88 | 4.02 | | | | |
| 2 deg C.-8 deg C. | 5.98 | | | | 6.03 | | | 6.15 | | | 6.28 | 6.13 | 6.22 | 6.11 | 6.18 |

TABLE 4

| | 0 day titer | 1 wk | 2 wk | 3 wk | 4 wk | 6 wk | 8 wk | 12 wk | 16 wk | 20 wk | 24 wk | 36 wk | 48 wk | 72 wk | 97 wk |
|---|---|---|---|---|---|---|---|---|---|---|---|---|---|---|---|
| Formulation details<br>Peptone Hydrolysed - 20% | | | | | | | | | | | | | | | |
| 37 deg C. | 6.13 | 5.93 | 4.75 | 3.21 | 1.13 | | | | | | | | | | |
| 25 deg C. | 6.13 | 6.18 | 6.23 | 6.31 | 6.08 | 6.1 | 6.15 | 5.98 | 5.55 | 5.28 | 4.94 | | | | |
| 2 deg C.-8 deg C. | 6.13 | | | | 6.19 | | | 6.22 | | | 6.08 | 6.01 | 5.99 | 6.11 | 6.23 |
| Formulation details<br>Peptone Hydrolysed - 20%<br>Trehalose - 1%<br>Fucose - 0.02% | | | | | | | | | | | | | | | |
| 37 deg C. | 6.31 | 6.11 | 4.59 | 3.34 | 2.32 | | | | | | | | | | |
| 25 deg C. | 6.31 | 6.28 | 6.13 | 6.01 | 6.05 | 5.95 | 6.21 | 6.38 | 5.75 | 5.52 | 5.22 | | | | |
| 2 deg C.-8 deg C. | 6.31 | | | | 6.35 | | | 6.28 | | | 6.17 | 5.93 | 6.12 | 6.22 | 6.31 |
| Formulation details<br>Egg protein hydrolysate - 20% | | | | | | | | | | | | | | | |
| 37 deg C. | 6.02 | 4.54 | 2.67 | 1.57 | | | | | | | | | | | |
| 25 deg C. | 6.02 | 6.17 | 6.19 | 6.08 | 5.97 | 5.18 | 4.37 | 3.68 | 2.54 | | | | | | |
| 2 deg C.-8 deg C. | 6.02 | | | | 6.18 | | | 6.23 | | | 6.29 | 6.11 | 5.93 | 6.12 | 6.24 |
| Formulation details<br>Egg protein hydrolysate - 20%<br>Trehalose0.5%<br>D-Sorbitol - 1%<br>Mannose - 0.5% | | | | | | | | | | | | | | | |
| 37 deg C. | 6.02 | 5.58 | 3.28 | 2.76 | 1.59 | | | | | | | | | | |
| 25 deg C. | 6.02 | 6.05 | 6.11 | 6.14 | 5.94 | 5.97 | 6.13 | 5.29 | 4.51 | 4.12 | | | | | |
| 2 deg C.-8 deg C. | 6.02 | | | | 6.23 | | | 6.12 | | | 6.28 | 6.33 | 6.15 | 6.01 | 6.17 |
| Formulation details<br>Lactalbumin Hydrolysate-20% | | | | | | | | | | | | | | | |
| 37 deg C. | 6.08 | 4.96 | 2.81 | 1.78 | 1.12 | | | | | | | | | | |
| 25 deg C. | 6.08 | 6.12 | 6.21 | 5.96 | 6.22 | 5.89 | 6.01 | 5.92 | 5.43 | 4.98 | 4.42 | | | | |
| 2 deg C.-8 deg C. | 6.08 | | | | 6.18 | | | 6.36 | | | 6.11 | 6.06 | 5.99 | 6.12 | 6.23 |

TABLE 4-continued

| | 0 day titer | 1 wk | 2 wk | 3 wk | 4 wk | 6 wk | 8 wk | 12 wk | 16 wk | 20 wk | 24 wk | 36 wk | 48 wk | 72 wk | 97 wk |
|---|---|---|---|---|---|---|---|---|---|---|---|---|---|---|---|
| Formulation details<br>Lactalbumin Hydrolysate - 20%<br>Trehalose - 0.5% | | | | | | | | | | | | | | | |
| 37 deg C. | 6.12 | 4.56 | 3.46 | 2.66 | 2.06 | 1.89 | 1.35 | | | | | | | | |
| 25 deg C. | 6.12 | 6.21 | 6.15 | 6.06 | 6.13 | 6.18 | 6.25 | 6.31 | 5.85 | 5.67 | 5.26 | | | | |
| 2 deg C.-8 deg C. | 6.12 | | | | 6.32 | | | 6.21 | | | 6.26 | 6.11 | 6.15 | 6.01 | 6.07 |
| Formulation details<br>Yeast Hydrolysate - 20% | | | | | | | | | | | | | | | |
| 37 deg C. | 6.22 | 6.01 | 3.35 | 1.76 | 0.83 | | | | | | | | | | |
| 25 deg C. | 6.22 | 6.1 | 6.23 | 6.03 | 6.13 | 5.76 | 5.28 | 5.18 | 5.02 | 4.89 | 4.24 | | | | |
| 2 deg C.-8 deg C. | 6.22 | | | | 6.28 | | | 6.45 | | | 6.16 | 6.04 | 6.15 | 6.27 | 6.35 |
| Formulation Details<br>Yeast Hydrolysate - 20%<br>Maltose - 5%<br>Lactose - 0.5% | | | | | | | | | | | | | | | |
| 37 deg C. | 5.98 | 6.03 | 3.45 | 2.58 | 1.52 | | | | | | | | | | |
| 25 deg C. | 5.98 | 6.13 | 6.32 | 6.22 | 6.18 | 6.23 | 6.31 | 5.98 | 5.38 | 4.88 | 4.02 | | | | |
| 2 deg C.-8 deg C. | 5.98 | | | | 6.03 | | | 6.15 | | | 6.28 | 6.13 | 6.22 | 6.11 | 6.18 |

Shown in FIGS. 13-17 is the stability data for the rotavirus 116E lyophilized formulations, F. Nos. 26-45, in each case at 2°-8° C. (A), 25° C. (B) and 37° C. (C).

This example demonstrates that some formulations are suitable for maintaining stability at 2°-8° C. for extended periods. It also demonstrates that some formulations are particularly suitable for storing at 25° C. or even 37° C.

All publications, patents and patent application publications, mentioned in the specification are indicative of the level of those skilled in the art to which this invention pertains. All publications, patents and patent applications are herein incorporated by reference to the same extent as if each individual publication or patent application was specifically and individually indicated to be incorporated by reference. Although the foregoing invention has been described in some detail by way of illustration and example for purposes of clarity of understanding, it will be obvious that certain changes and modifications may be practiced within the scope of the appended claims.

We claim:

1. A liquid vaccine composition for treatment and prophylaxis of rotavirus infections consisting of:

a. a pre-conditioned live attenuated rotavirus 116E, wherein the said live attenuated rotavirus 116E is infected in Vero cells supplemented with Human Serum Albumin capable of exhibiting a minimum of 0.8 log to a maximum of 1.1 logs per 0.5 ml enhanced titer as compared to typical live attenuated rotavirus 116E supplemented without Human Serum Albumin;

b. a pharmaceutically acceptable buffer consisting of HEPES Buffer in the range of 0.1 mM to 1000 mM of pH 6.8 to 8.0;

c. a non viral protein which is soy protein in the range of 0.05% to 50% w/v;

d. polyvinyl pyrollidine at a range of 0.25% to 5% w/v; and, e. pyridoxine HCl at 0.25% to 5% w/v, wherein the liquid vaccine composition does not contain Human Serum Albumin or any other supplemental stabilizer.

2. The liquid composition of claim 1, wherein the composition is stable for 24 months at 2°-8° C.

3. A method for producing a live attenuated rotavirus of claim 1 comprising:

(i) infecting host cells with a live attenuated rotavirus;

(ii) growing the infected cells in a cell culture medium capable of supporting the growth of said cells, wherein said medium is supplemented with a human serum albumin; and (iii) harvesting said rotavirus which is capable of exhibiting better stability from the cell culture medium.

* * * * *